United States Patent
Yu et al.

(10) Patent No.: US 12,091,454 B2
(45) Date of Patent: Sep. 17, 2024

(54) HUMANIZED ANTI-HUMAN NEUROTENSIN RECEPTOR 1 ANTIBODIES AND THEIR USES

(71) Applicants: DEVELOPMENT CENTER FOR BIOTECHNOLOGY, New Taipei (TW); NATIONAL HEALTH RESEARCH INSTITUTES, Miaoli County (TW)

(72) Inventors: Cheng-Chou Yu, Taipei (TW); Shu-Ping Yeh, Taipei (TW); Chao-Yang Huang, Taipei (TW); Szu-Liang Lai, Taipei (TW); Shih-Liang Hsiao, Taipei (TW); Mei-Ling Hou, Taipei (TW); Tzung-Jie Yang, Taipei (TW); Wei-Ting Sun, Taipei (TW); Liang-Yu Hsia, Taipei (TW); Andrew Yueh, Miaoli County (TW); Chiung-Tong Chen, Miaoli County (TW); Ren-Huang Wu, Miaoli County (TW); Pei-Shan Wu, Miaoli County (TW); Han-Shu Hu, Miaoli County (TW); Tzu-Chin Wu, Miaoli County (TW); Jia-Ni Tian, Miaoli County (TW)

(73) Assignees: DEVELOPMENT CENTER FOR BIOTECHNOLOGY, New Taipei (TW); NATIONAL HEALTH RESEARCH INSTITUTES, Miaoli County (TW)

( * ) Notice: Subject to any disclaimer, the term of this patent is extended or adjusted under 35 U.S.C. 154(b) by 0 days.

(21) Appl. No.: 18/089,812

(22) Filed: Dec. 28, 2022

(65) Prior Publication Data
US 2024/0218062 A1 Jul. 4, 2024

(51) Int. Cl.
*C07K 16/28* (2006.01)
*A61P 35/00* (2006.01)
*C12N 15/63* (2006.01)

(52) U.S. Cl.
CPC ............ *C07K 16/28* (2013.01); *A61P 35/00* (2018.01); *C12N 15/63* (2013.01); *C07K 2317/24* (2013.01); *C07K 2317/31* (2013.01)

(58) Field of Classification Search
None
See application file for complete search history.

(56) References Cited

U.S. PATENT DOCUMENTS

| | | | |
|---|---|---|---|
| 5,925,661 | A | 7/1999 | Labeeuw et al. |
| 8,586,043 | B2 | 11/2013 | Forgez et al. |
| 8,771,691 | B2 | 7/2014 | Forgez et al. |
| 9,868,707 | B2 | 1/2018 | Pinkerton et al. |
| 10,118,902 | B2 | 11/2018 | Pinkerton et al. |
| 10,799,605 | B2 | 10/2020 | Osterkamp et al. |
| 2015/0299133 | A1 | 10/2015 | Osterkamp et al. |
| 2016/0369005 | A1* | 12/2016 | Lippincott et al. |
| 2018/0134788 | A1 | 5/2018 | Forgez et al. |
| 2020/0087697 | A1* | 3/2020 | Tsai et al. |
| 2020/0140530 | A1 | 5/2020 | Burton et al. |
| 2021/0213118 | A1 | 7/2021 | Marsault et al. |

FOREIGN PATENT DOCUMENTS

| | | |
|---|---|---|
| CN | 101472601 A | 7/2009 |
| CN | 104744439 A | 7/2015 |
| CN | 104744375 B | 9/2017 |
| CN | 104744455 B | 3/2018 |
| EP | 2954934 A1 | 12/2015 |
| TW | WO2021/252578 * | 12/2021 |
| TW | 1781647 B | 10/2022 |
| WO | 2011/156557 A2 | 12/2011 |
| WO | 2020/041896 A1 | 3/2020 |
| WO | 2020/053147 A1 | 3/2020 |
| WO | 2021/252578 A1 | 12/2021 |

OTHER PUBLICATIONS

Boonyaratanakornkita et al Monoclonal antibodies for prophylaxis and treatment of respiratory viral infections. Curr Opin Infect Dis. 2022; 35(4):280-287 (Year: 2022).*
Nikolaou et al The role of Neurotensin and its receptors in non-gastrointestinal cancers: a review. Cell Commun Signal. 2020; 18(68) (Year: 2020).*
Ouyang et al Oncogenic role of neurotensin and neurotensin receptors in various cancers. Clin Exp Pharmacol Physiol. 2017; 44: 841-846] (Year: 2017).*
Vajdos et al Comprehensive Functional Maps of the Antigen binding Site of an Anti-ErbB2 Antibody Obtained with Shotgun Scanning Mutagenesis. J Mol Biol. 2002; 320(2):415-428 (Year: 2002).*
Wu et al Neurotensin and its high affinity receptor 1 as a potential pharmacological target in cancer therapy. Front Endocrinol (Lausanne). 2013; 3(184)] (Year: 2013).*
Minnix et al Improved targeting of an anti-TAG-72 antibody drug conjugate for the treatment of ovarian cancer. Cancer Med 2020 9 (13):4756-4767]. (Year: 2020).*
Rafiq et al Targeted delivery of a PD-1-blocking scFv by CAR-T cells enhances anti-tumor efficacy in vivo. Nat Biotechnol. Oct. 2018 ; 36(9): 847-856 (Year: 2018).*
Muhammed The Best IgG Subclass for the Development of Therapeutic Monoclonal Antibody Drugs and their Commercial Production: A Review. Immunome Res. 2020; 16:173] (Year: 2020).*

(Continued)

*Primary Examiner* — Daniel E Kolker
*Assistant Examiner* — Lea S O'Brien
(74) *Attorney, Agent, or Firm* — LADAS & PARRY LLP

(57) ABSTRACT

A humanized anti-neurotensin receptor 1 (NTSR1) antibody or an antigen-binding fragment thereof. Also, a method for treating, prophylactic treating and/or preventing diseases and/or disorders caused by or related to NTSR1 activity and/or signaling, and a method or kit for detecting NTSR1 in a sample.

19 Claims, 15 Drawing Sheets
Specification includes a Sequence Listing.

(56) References Cited

OTHER PUBLICATIONS

Kaneko et al.Chimeric Anti-Human Podoplanin Antibody NZ-12 of Lambda Light Chain Exerts Higher Antibody-Dependent Cellular Cytotoxicity and Complement-Dependent Cytotoxicity Compared with NZ-8 of Kappa Light Chain. Monoclonal Antibodies in Immunodiagnosis and Immunotherapy 2017; 36(1):25-29] (Year: 2017).*
Cheng-chou et al. Humanized Anti-Human Neurotensin Receptor 1 Antibodies and Their Uses. Dec. 28, 2022. PCT/US22/82472.*
Li et al., Antitumor activity of EGFR-specific CAR T cells against non-small-cell lung cancer cells in vitro and in mice, 2018, Cell Death and Disease, vol. 9, No. 177, pp. 2-11.*
Bozou JC, Amar S, Vincent JP, Kitabgi P (1986) Neurotensin-mediated inhibition of cyclic AMP formation in neuroblastoma N1E115 cells: involvement of the inhibitory GTP-binding component of adenylate cyclase. Mol Pharmacol 29: 489-496.
Dupouy S, Viardot-Foucault V, Alifano M, Souaze F, Plu-Bureau G, Chaouat M, Lavaur A, Hugol D, Gespach C, Gompel A et al (2009) The neurotensin receptor-1 pathway contributes to human ductal breast cancer progression. PLoS One 4: e4223.
Ehlers RA, Zhang Y, Hellmich MR, Evers BM (2000) Neurotensin-mediated activation of MAPK pathways and AP-1 binding in the human pancreatic cancer cell line, MIA PaCa-2. Biochem Biophys Res Commun 269: 704-708.
Hwang JR, Baek MW, Sim J, Choi HS, Han JM, Kim YL, Hwang JI, Kwon HB, Beaudet N, Sarret P et al (2010) Intermolecular cross-talk between NTR1 and NTR2 neurotensin receptor promotes intracellular sequestration and functional inhibition of NTR1 receptors. Biochem Biophys Res Commun 391: 1007-1013.
Jemal A, Bray F, Center MM, Ferlay J, Ward E, Forman D (2011) Global cancer statistics. CA Cancer J Clin 61: 69-90.
Muller KM, Tveteraas IH, Aasrum M, Odegard J, Dawood M, Dajani O, Christoffersen T, Sandnes DL (2011) Role of protein kinase C and epidermal growth factor receptor signalling in growth stimulation by neurotensin in colon carcinoma cells. BMC Cancer 11: 421.
Najimi M, Maloteaux JM, Hermans E (2002) Cytoskeleton-related trafficking of the EAAC1 glutamate transporter after activation of the G(q/11)-coupled neurotensin receptor NTS1. Febs Lett 523: 224-228.
Najimi M, Souaze F, Mendez M, Hermans E, Berbar T, Rostene W, Forgez P (1998) Activation of receptor gene transcription is required to maintain cell sensitization after agonist exposure. Study on neurotensin receptor. J Biol Chem 273: 21634-21641.
Poinot-Chazel C, Portier M, Bouaboula M, Vita N, Pecceu F, Gully D, Monroe JG, Maffrand JP, Le Fur G, Casellas P (1996) Activation of mitogen-activated protein kinase couples neurotensin receptor stimulation to induction of the primary response gene Krox-24. Biochem J 320 ( Pt 1): 145-151.
Seufferlein T, Rozengurt E (1996) Galanin, neurotensin, and phorbol esters rapidly stimulate activation of mitogen-activated protein kinase in small cell lung cancer cells. Cancer Res 56: 5758-5764.
Shimizu S, Tsukada J, Sugimoto T, Kikkawa N, Sasaki K, Chazono H, Hanazawa T, Okamoto Y, Seki N (2008) Identification of a novel therapeutic target for head and neck squamous cell carcinomas: a role for the neurotensin-neurotensin receptor 1 oncogenic signaling pathway. Int J Cancer 123: 1816-1823.
Snider RM, Forray C, Pfenning M, Richelson E (1986) Neurotensin stimulates inositol phospholipid metabolism and calcium mobilization in murine neuroblastoma clone N1E-115. J Neurochem 47: 1214-1218.
Somai S, Gompel A, Rostene W, Forgez P (2002) Neurotensin counteracts apoptosis in breast cancer cells. Biochem Biophys Res Commun 295: 482-488.
Souaze F, Forgez P (2006) Molecular and cellular regulation of neurotensin receptor under acute and chronic agonist stimulation. Peptides 27: 2493-2501.
Tanaka K (1990) Structural studies of amorphous Se under pressure. Phys Rev B Condens Matter 42: 11245-11251.
Theodorsson-Norheim E, Oberg K, Rosell S, Bostrom H (1983) Neurotensinlike immunoreactivity in plasma and tumor tissue from patients with endocrine tumors of the pancreas and gut. Gastroenterology 85: 881-889.
Toy-Miou-Leong M, Bachelet CM, Pelaprat D, Rostene W, Forgez P (2004) NT agonist regulates expression of nuclear high-affinity neurotensin receptors. J Histochem Cytochem 52: 335-345.
Turner JT, James-Kracke MR, Camden JM (1990) Regulation of the neurotensin receptor and intracellular calcium mobilization in HT29 cells. J Pharmacol Exp Ther 253: 1049-1056.
Vias M, Burtt G, Culig Z, Veerakumarasivam A, Neal DE, Mills IG (2007) A role for neurotensin in bicalutamide resistant prostate cancer cells. Prostate 67: 190-202.
Wang HL, Wu T (1996) G alpha q/11 mediates neurotensin excitation of substantia nigra dopaminergic neurons. Brain Res Mol Brain Res 36: 29-36.
Woodworth HL, Perez-Bonilla PA, Beekly BG, Lewis TJ, Leinninger GM (2018) Identification of Neurotensin Receptor Expressing Cells in the Ventral Tegmental Area across the Lifespan. eNeuro 5.
Zherui_Wu, et al.: (2012) Neurotensin and its high affinity receptor 1 as a potential pharmacological target in cancer therapy. Front Endocrinol (Lausanne) 3: 184.
ISR for International Application PCT/US22/82472 mailed Aug. 10, 2023.
Written Opinion for International Application PCT/US22/82472 mailed Aug. 10, 2023.
Taiwanese Office Action dated Dec. 7, 2023 for corresponding TW Patent Application No. 111150483.
Taiwanese Search Report dated Dec. 7, 2023 for corresponding TW Patent Application No. 111150483.

* cited by examiner

Primary Alignment of $V_L$ Segments

```
Kabat        1        5        10       15       20                    35        40
m7C3         DVLMTQTPLSLPVSLGDQASISC[RSSQSIVHSNGNTYLE]WYLQKP
VKI          DIQMTQSPSSLSASVGDRVTITC[RASQDVNTAVA-----]WYQQKP
                                        CDR-1

Kabat        45                        60       65       70       75       80       85
m7C3         GQSPKLLIY[KVSNRFS]GVPDRFSGSGSGTDFTLKISRVEAEDLGVY
VKI          GKAPKLLIY[SASFLES]GVPSRFSGSGSGTDFTLTISSLQPEDFATY
                       CDR-2

Kabat                  100      104
m7C3         YC[FQGSHLPWT]FGGGTKLEIKR    (SEQ ID NO:8)
VKI          YC[QQHYTTPPT]FGQGTKVEIKR    (SEQ ID NO:24)
                CDR-3
``` m7C3 : *Mus musculus*: IGKV1
Human template(4d5): IGKV1

FIG. 1A

Primary Alignment of V$_H$ Segments

```
Kabat         1           5          10          15          20          25          CDR-1        36    40
m7C3          QVQLQQPGSVLVRPGDSVMLSCKAAS[GYTFTSSWIH]WAKQRPGQG
VH III        EVQLVESGGGLVQPGGSLRLSCAAS[GFTFSDTYIH]WVRQAPGKG Kabat         45                      CDR-2                    66          70          75          80 82A B C
m7C3          PEWIG[QIRPNSGNTYYNEKFKV]KATLTVDTSSSTAYVDLSSLTS
VH III        LEWVA[RIYPTNGYTRYADSVKG]RFTISRDDSKNTLYLQMNSLRA Kabat         85          90    93 94    CDR-3                105         110
m7C3          EDSAVYYCAR[YYYGFDY----]WGQGTTVTVSS (SEQ ID NO:7)
VH III        EDTAVYYCAR[WGGDGFYAMDV]WGQGTLVTVSS (SEQ ID NO:25)
``` m7C3: *Mus musculus*: IGHV1
Human template(4d5): IGHV3

FIG. 1B

Primary Alignment of $V_L$ Segments

```
Kabat      1       5        10        15       20                      CDR-1              35        40
m7C3       DVLMTQTPLSLPVSLGDQASISC[RSSQSIVHSNGNTYLE]WYLQKP
VKII       DIVMTQTPLSLSVTPGQPASISC[KSSQSLLHSDGKTYLY]WYLQKP Kabat            45                   CDR-2          60        65         70        75        80        85
m7C3       GQSPKLLIY[KVSNRFS]GVPDRFSGSGSGTDFTLKISRVEAEDLGVY
VKII       GQSPQLLIY[EVSSRFS]GVPDRFSGSGSGTDFTLKISRVEAEDVGVY Kabat            CDR-3       100   104
m7C3       YC[FQGSHLPWT]FGGGTKLEIKR  (SEQ ID NO: 8)
VKII       YC[QQYSGYPLT]FGQGTKVEIKR  (SEQ ID NO: 26)
``` m7C3 : *Mus musculus*: IGKV1
Human template(IMGT): IGVK2

FIG. 2A

Primary Alignment of V$_H$ Segments

```
Kabat    1       5        10        15        20        25           CDR-1       36    40
m7C3     QVQLQQPGSVLVRPGDSVMLSCKAS[GYTFTSSWIH]WAKQRPGQG
VHI      QVQLVQSGAEVKKPGASVKVSCKAS[GYTFTGYYMH]WVRQAPGQG Kabat    45                          CDR-2                    66        70        75            80 82 a b c
m7C3     PEWIG[QIRPNSGNTYYNEKFKV]KATLTVDTSSSTAYVDLSSLTS
VHI      LEWMG[IINPSGGSTSYAQKFQG]RVTMTRDTSTSTVYMELSSLRS Kabat    85       90    9394        CDR-3              105       110
m7C3     EDSAVYYCAR[YYYGFDY----]WGQGTTVTVSS    (SEQ ID NO: 7)
VHI      EDTAVYYCAR[WGGDGFYAMDV]WGQGTLVTVSS    (SEQ ID NO: 27)
``` m7C3 : *Mus musculus*: IGHV1
Human template(IMGT): IGHV1

FIG. 2B

Compare the amino acids change in V$_H$ of 7C3, AKT2 and humanized sequences (HU)

|  | FW1 | CDR1 | FW2 |
|---|---|---|---|
| MOUSE 7C3 VH | QVQLQQPGSVLVRPGDSVMLSCKAS | GYTFTSSWIH | WAKQRPGQGPEWIG |
| AKT2_VH | QVQLQQPGSVLVRPGASVMLSCKAS | GYAFTSSWIH | WAKQRPGQGLEWIG |
| 7C3 HUVH | QVQLVQSGAEVKKPGASVKVSCKAS | GYTFTSSWIH | WVRQAPGQGLEWMG |
| AKT2 HUVH | QVQLVQSGAEVKKPGASVKVSCKAS | GYAFTSSWIH | WVRQAPGQGLEWMG |
| *Kabat no. |  | 28 |  |

|  | CDR2 | FW3 | CDR3 | FW4 |
|---|---|---|---|---|
| MOUSE 7C3 VH | QIRPNSGNTYYNEKFKV | KATLTVDTSSSTAYVDLSSLTSEDSAVYYCAR | YYYGFDY | WGQGTLVTVSS |
| AKT2_VH | QIRPNSGNTYYNEKFKV | KATLTVDTSSSTAYVDLSSLTSEDSAVYYCAR | YHYGFDY | WGQGTLVTVSS |
| 7C3 HUVH | QIRPNSGNTYYNEKFKV | RVTMTRDTSTSTVYMELSSLRSEDTAVYYCAR | YYYGFDY | WGQGTLVTVSS |
| AKT2 HUVH | QIRPNSGNTYYNEKFKV | RVTMTRDTSTSTVYMELSSLRSEDTAVYYCAR | YHYGFDY | WGQGTLVTVSS |
| *Kabat no. |  |  | 96 |  |

*: Residue numbers are according to kabat nomenclature.

FIG. 6A

Compare the amino acids change in $V_L$ of 7C3, AKT2 and humanized sequences (HU)

| | FW1 | CDR1 | FW2 |
|---|---|---|---|
| MOUSE 7C3 VL | DVLMTQTPLSLPVSLGDQASISC | RSSQSIVHSNGNTYLE | WYLQKPGQSPKLLIY |
| AKT2_VL | DVLMTQTPLSLPVSLGDQASISC | RSSQSIVHSNGNTYLE | WYLQKPGQSPKLLIY |
| 7C3 HUVL | DIVMTQTPLSLSVTPGQPASISC | RSSQSIVHSNGNTYLE | WYLQKPGQSPQLLIY |
| AKT2 HUVL | DIVMTQTPLSLSVTPGQPASISC | RSSQSIVHSNGNTYLE | WYLQKPGQSPQLLIY |

| | CDR2 | FW3 | CDR3 | FW4 |
|---|---|---|---|---|
| MOUSE 7C3 VL | KVSNRFS | GVPDRFSGSGSGTDFTLKISRVEAEDLGVYYC | FQGSHLPWT | FGGGTKLEIK |
| AKT2_VL | KVSNRFS | GVPDRFSGSGSGTDFTLKISRVEAEDLGVYYC | FQGAHLPWT | FGGGTKLEIK |
| 7C3 HUVL | KVSNRFS | GVPDRFSGSGSGTDFTLKISRVEAEDVGVYYC | FQGSHLPWT | FGQGTKVEIK |
| AKT2 HUVL | KVSNRFS | GVPDRFSGSGSGTDFTLKISRVEAEDVGVYYC | FQGAHLPWT | FGQGTKVEIK |
| *Kabat no. | | | 92 | |

*: Residue numbers are according to kabat nomenclature.

FIG. 6B

Compare the amino acids change in $V_L$ of 7C3, AKT2 and humanized sequences (HD)

|  | FW1 | CDR1 | FW2 |
|---|---|---|---|
| MOUSE 7C3 VL | DVLMTQTPLSLPVSLGDQASISC | RSSQSIVHSNGNTYLE | WYLQKPGQSPKLLIY |
| AKT2_VL | DVLMTQTPLSLPVSLGDQASISC | RSSQSIVHSNGNTYLE | WYLQKPGQSPKLLIY |
| 7C3 HDVL | DIQMTQSPSSLSASVGDRVTITC | RSSQSIVHSNGNTYLE | WYQQKPGKAPKLLIY |
| AKT2 HDVL | DIQMTQSPSSLSASVGDRVTITC | RSSQSIVHSNGNTYLE | WYQQKPGKAPKLLIY |

|  | CDR2 | FW3 | CDR3 | FW4 |
|---|---|---|---|---|
| MOUSE 7C3 VL | KVSNRFS | GVPDRFSGSGSGTDFTLKISRVEAEDLGVYYC | FQGSHLPWT | FGGGTKLEIK |
| AKT2_VL | KVSNRFS | GVPDRFSGSGSGTDFTLKISRVEAEDLGVYYC | FQGAHLPWT | FGGGTKLEIK |
| 7C3 HDVL | KVSNRFS | GVPSRFSGSGSGTDFTLTISSLQPEDFATYYC | FQGSHLPWT | FGGGTKVEIK |
| AKT2 HDVL | KVSNRFS | GVPSRFSGSGSGTDFTLTISSLQPEDFATYYC | FQGAHLPWT | FGGGTKVEIK |

*Kabat no.      92

*: Residue numbers are according to kabat nomenclature.

FIG. 6C

```
                         SEQUENCE LISTING

Sequence total quantity: 27
SEQ ID NO: 1            moltype = AA   length = 10
FEATURE                 Location/Qualifiers
source                  1..10
                        mol_type = protein
                        organism = synthetic construct
SEQUENCE: 1
GYTFTSSWIH                                                                 10

SEQ ID NO: 2            moltype = AA   length = 17
FEATURE                 Location/Qualifiers
source                  1..17
                        mol_type = protein
                        organism = synthetic construct
SEQUENCE: 2
QIRPNSGNTY YNEKFKV                                                         17

SEQ ID NO: 3            moltype = AA   length = 7
FEATURE                 Location/Qualifiers
source                  1..7
                        mol_type = protein
                        organism = synthetic construct
SEQUENCE: 3
YYYGFDY                                                                    7

SEQ ID NO: 4            moltype = AA   length = 16
FEATURE                 Location/Qualifiers
source                  1..16
                        mol_type = protein
                        organism = synthetic construct
SEQUENCE: 4
RSSQSIVHSN GNTYLE                                                          16

SEQ ID NO: 5            moltype = AA   length = 7
FEATURE                 Location/Qualifiers
source                  1..7
                        mol_type = protein
                        organism = synthetic construct
SEQUENCE: 5
KVSNRFS                                                                    7

SEQ ID NO: 6            moltype = AA   length = 9
FEATURE                 Location/Qualifiers
source                  1..9
                        mol_type = protein
                        organism = synthetic construct
SEQUENCE: 6
FQGSHLPWT                                                                  9

SEQ ID NO: 7            moltype = AA   length = 116
FEATURE                 Location/Qualifiers
source                  1..116
                        mol_type = protein
                        organism = synthetic construct
SEQUENCE: 7
QVQLQQPGSV LVRPGDSVML SCKASGYTFT SSWIHWAKQR PGQGPEWIGQ IRPNSGNTYY           60
NEKFKVKATL TVDTSSSTAY VDLSSLTSED SAVYYCARYY YGFDYWGQGT TVTVSS              116
```

```
SEQ ID NO: 8              moltype = AA   length = 112
FEATURE                   Location/Qualifiers
source                    1..112
                          mol_type = protein
                          organism = synthetic construct
SEQUENCE: 8
DVLMTQTPLS LPVSLGDQAS ISCRSSQSIV HSNGNTYLEW YLQKPGQSPK LLIYKVSNRF    60
SGVPDRFSGS GSGTDFTLKI SRVEAEDLGV YYCFQGSHLP WTFGGGTKLE IK           112

SEQ ID NO: 9              moltype = AA   length = 116
FEATURE                   Location/Qualifiers
source                    1..116
                          mol_type = protein
                          organism = synthetic construct
SEQUENCE: 9
QVQLQQPGSV LVRPGASVKL SCKASGYAFT SSWIHWAKQR PGQGLEWIGQ IRPNSGNTYY    60
NEKFKVKATL TVDTSSSTAY VDLSSLTSED SAVYYCARYH YGFDYWGQGT LVTVSS       116

SEQ ID NO: 10             moltype = AA   length = 112
FEATURE                   Location/Qualifiers
source                    1..112
                          mol_type = protein
                          organism = synthetic construct
SEQUENCE: 10
DVLMTQTPLS LPVSLGDQAS ISCRSSQSIV HSNGNTYLEW YLQKPGQSPK LLIYKVSNRF    60
SGVPDRFSGS GSGTDFTLKI SRVEAEDLGV YYCFQGAHLP WTFGGGTKLE IK           112

SEQ ID NO: 11             moltype = AA   length = 116
FEATURE                   Location/Qualifiers
source                    1..116
                          mol_type = protein
                          organism = synthetic construct
SEQUENCE: 11
EVQLVESGGG LVQPGGSLRL SCAASGYTFT SSWIHWVRQA PGKGLEWVAQ IRPNSGNTYY    60
NEKFKVRFTI SRDDSKNTLY LQMNSLRAED TAVYYCARYY YGFDYWGQGT LVTVSS       116

SEQ ID NO: 12             moltype = AA   length = 112
FEATURE                   Location/Qualifiers
source                    1..112
                          mol_type = protein
                          organism = synthetic construct
SEQUENCE: 12
DIQMTQSPSS LSASVGDRVT ITCRSSQSIV HSNGNTYLEW YQQKPGKAPK LLIYKVSNRF    60
SGVPSRFSGS GSGTDFTLTI SSLQPEDFAT YYCFQGSHLP WTFGQGTKVE IK           112

SEQ ID NO: 13             moltype = AA   length = 116
FEATURE                   Location/Qualifiers
source                    1..116
                          mol_type = protein
                          organism = synthetic construct
SEQUENCE: 13
QVQLVQSGAE VKKPGASVKV SCKASGYTFT SSWIHWVRQA PGQGLEWMGQ IRPNSGNTYY    60
NEKFKVRVTM TRDTSTSTVY MELSSLRSED TAVYYCARYY YGFDYWGQGT LVTVSS       116

SEQ ID NO: 14             moltype = AA   length = 112
FEATURE                   Location/Qualifiers
source                    1..112
                          mol_type = protein
                          organism = synthetic construct
SEQUENCE: 14
DIVMTQTPLS LSVTPGQPAS ISCRSSQSIV HSNGNTYLEW YLQKPGQSPQ LLIYKVSNRF    60
SGVPDRFSGS GSGTDFTLKI SRVEAEDVGV YYCFQGSHLP WTFGQGTKVE IK           112

SEQ ID NO: 15             moltype = AA   length = 112
FEATURE                   Location/Qualifiers
source                    1..112
                          mol_type = protein
                          organism = synthetic construct
SEQUENCE: 15
DIQMTQSPSS LSASVGDRVT ITCRSSQSIV HSNGNTYLEW YQQKPGKAPK LLIYKVSNRF    60
SGVPSRFSGS GSGTDFTLTI SSLQPEDFAT YYCFQGAHLP WTFGQGTKVE IK           112

SEQ ID NO: 16             moltype = AA   length = 116
FEATURE                   Location/Qualifiers
source                    1..116
                          mol_type = protein
                          organism = synthetic construct
SEQUENCE: 16
```

```
QVQLVQSGAE VKKPGASVKV SCKASGYAFT SSWIHWVRQA PGQGLEWMGQ IRPNSGNTYY    60
NEKFKVRVTM TRDTSTSTVY MELSSLRSED TAVYYCARYH YGFDYWGQGT LVTVSS       116

SEQ ID NO: 17           moltype = AA  length = 112
FEATURE                 Location/Qualifiers
source                  1..112
                        mol_type = protein
                        organism = synthetic construct
SEQUENCE: 17
DIVMTQTPLS LSVTPGQPAS ISCRSSQSIV HSNGNTYLEW YLQKPGQSPQ LLIYKVSNRF    60
SGVPDRFSGS GSGTDFTLKI SRVEAEDVGV YYCFQGAHLP WTFGQGTKVE IK           112

SEQ ID NO: 18           moltype = AA  length = 10
FEATURE                 Location/Qualifiers
source                  1..10
                        mol_type = protein
                        organism = synthetic construct
SEQUENCE: 18
GYAFTSSWIH                                                           10

SEQ ID NO: 19           moltype = AA  length = 17
FEATURE                 Location/Qualifiers
source                  1..17
                        mol_type = protein
                        organism = synthetic construct
SEQUENCE: 19
QIRPNSGNTY YNEKFKV                                                   17

SEQ ID NO: 20           moltype = AA  length = 7
FEATURE                 Location/Qualifiers
source                  1..7
                        mol_type = protein
                        organism = synthetic construct
SEQUENCE: 20
YHYGFDY                                                              7

SEQ ID NO: 21           moltype = AA  length = 16
FEATURE                 Location/Qualifiers
source                  1..16
                        mol_type = protein
                        organism = synthetic construct
SEQUENCE: 21
RSSQSIVHSN GNTYLE                                                    16

SEQ ID NO: 22           moltype = AA  length = 7
FEATURE                 Location/Qualifiers
source                  1..7
                        mol_type = protein
                        organism = synthetic construct
SEQUENCE: 22
KVSNRFS                                                              7

SEQ ID NO: 23           moltype = AA  length = 9
FEATURE                 Location/Qualifiers
source                  1..9
                        mol_type = protein
                        organism = synthetic construct
SEQUENCE: 23
FQGAHLPWT                                                            9

SEQ ID NO: 24           moltype = AA  length = 108
FEATURE                 Location/Qualifiers
source                  1..108
                        mol_type = protein
                        organism = Homo sapiens
SEQUENCE: 24
DIQMTQSPSS LSASVGDRVT ITCRASQDVN TAVAWYQQKP GKAPKLLIYS ASFLESGVPS    60
RFSGSGSGTD FTLTISSLQP EDFATYYCQQ HYTTPPTFGQ GTKVEIKR                 108

SEQ ID NO: 25           moltype = AA  length = 120
FEATURE                 Location/Qualifiers
source                  1..120
                        mol_type = protein
                        organism = Homo sapiens
SEQUENCE: 25
EVQLVESGGG LVQPGGSLRL SCAASGFTFS DTYIHWVRQA PGKGLEWVAR IYPTNGYTRY    60
ADSVKGRFTI SRDDSKNTLY LQMNSLRAED TAVYYCARWG GDGFYAMDVW GQGTLVTVSS   120

SEQ ID NO: 26           moltype = AA  length = 113
```

```
FEATURE             Location/Qualifiers
source              1..113
                    mol_type = protein
                    organism = Homo sapiens
SEQUENCE: 26
DIVMTQTPLS LSVTPGQPAS ISCKSSQSLL HSDGKTYLYW YLQKPGQSPQ LLIYEVSSRF  60
SGVPDRFSGS GSGTDFTLKI SRVEAEDVGV YYCQQYSGYP LTFGQGTKVE IKR        113

SEQ ID NO: 27       moltype = AA  length = 120
FEATURE             Location/Qualifiers
source              1..120
                    mol_type = protein
                    organism = Homo sapiens
SEQUENCE: 27
QVQLVQSGAE VKKPGASVKV SCKASGYTFT GYYMHWVRQA PGQGLEWMGI INPSGGSTSY  60
AQKFQGRVTM TRDTSTSTVY MELSSLRSED TAVYYCARWG GDGFYAMDVW GQGTLVTVSS  120
```

HUMANIZED ANTI-HUMAN NEUROTENSIN RECEPTOR 1 ANTIBODIES AND THEIR USES

REFERENCE TO SEQUENCE LISTING SUBMITTED VIA EFS-WEB

This application includes an electronically submitted sequence listing in .xml format. The .xml fie contains a sequence listing entitled "3_US13111_SequenceListing.xml" created on Dec. 28, 2022 and is 25,857 bytes in size. The sequence listing contained in this .xml file is part of the specification and is hereby incorporated by reference herein in its entirety.

FIELD OF THE INVENTION

The present disclosure relates to novel humanized antibodies, particularly to humanized antibodies which bind specifically to human neurotensin receptor 1 (NTSR1). The present disclosure also relates to uses of such antibodies for suppressing tumor growth and metastasis.

BACKGROUND OF THE INVENTION

The ligand of NTSR1 is widely studied. The NTSR1 comprises 424 amino acids and has a high affinity for NTS. The NTSR1 has been identified in the brain and in various cancer cells. The signaling pathways induced by the NTS/NTSR1 complex have been studied in different cellular types, such as N1E-115, HT-29, and NTSR1-transfected CHO overexpressing NTSR1. The NTS/NTSR1 complex leads to phospholipase C (PLC) activation with subsequent production of inositol triphosphate (IP3) and diacylglycerol (DAG) from membrane phospholipids. The activation of PLC leads to the production of inositol triphosphate (IP3) and diacylglycerol from membrane phospholipids (PIP2). These two second messengers induce the activation of PKC and the mobilization of intracellular calcium which are key oncogenic effectors.

Several signaling pathways potentially involved in cell proliferation, survival, migration, and invasion are described after NTSR1 stimulation. The signaling mechanisms mediating the effects of neurotensinergic system involve multiple pathways and are cell-dependent. NTS/NTSR1 complex was demonstrated which could enhance cancer progression in aggressive malignant solid tumors such as mesothelioma, non-small-cell lung, liver, breast, and head and neck squamous carcinomas. NTSR1 is a promising molecular marker for non-small-cell lung and prostate cancer based on patient tissue staining. It had previously shown the presence of a chronic self-activation loop between neurotensin and NTSR1, as one mechanism responsible for the constitutive activation of the mitogen-activated protein kinase mitogenic signaling pathways along with sustained target gene activation. More recently, NTSR1 expression level was found to be associated with poor prognosis in patients with ductal breast cancer, and similar results have been found in head and neck squamous cell carcinomas.

Thus, NTSR1 is a potential target for cancer therapy. The carcinogenesis and cancer recurrence may be reduced via inhibiting the activity of NTSR1.

SUMMARY OF THE INVENTION

Embodiments of the disclosure relate to humanized anti-NTSR1 antibodies that specifically bind human NTSR1, as well as methods of using such antibodies in treatment of cancers. By specifically binding NTSR1, antibodies as disclosed herein are able to be used to treat cancers that overexpress NTSR1, including various epithelial cancers.

Accordingly, the present disclosure provides a humanized anti-NTSR1 antibody or an antigen-binding fragment thereof, including:

a heavy chain variable region ($V_H$) comprising the sequence of SEQ ID NO: 16, 11 or 13, or a sequence with at least about 90% identity to the sequence of SEQ ID NO: 16, 11 or 13; and a light chain variable region ($V_L$) comprising the sequence of SEQ ID NO: 17, 15, 12 or 14, or a sequence with at least about 90% identity to the sequence of SEQ ID NO: 17, 15, 12 or 14.

In one embodiment of the present disclosure, the $V_H$ comprises the sequence of SEQ ID NO: 16, and the $V_L$ comprises the sequence of SEQ ID NO: 17 or 15.

In another embodiment of the present disclosure, the $V_H$ comprises the sequence of SEQ ID NO: 13, and the $V_L$ comprises the sequence of SEQ ID NO: 12 or 14.

In still another embodiment of the present disclosure, the $V_H$ comprises the sequence of SEQ ID NO: 11, and the $V_L$ comprises the sequence of SEQ ID NO: 12 or 14.

In some embodiments of the present disclosure, the humanized anti-NTSR1 antibody has a heavy chain constant region selected from the group consisting of IgGI, IgG2 and IgG4 isoforms, and a light chain constant region selected from the group consisting of κ and λ isotypes.

In some embodiments of the present disclosure, the humanized anti-NTSR1 antibody or the antigen-binding fragment thereof is an Fab fragment, an F(ab')$_2$ fragment, an ScFv fragment, a chimeric antibody, or a nanobody.

In some embodiments of the present disclosure, the humanized anti-NTSR1 antibody or the antigen-binding fragment thereof is multi-specific.

The present disclosure also provides an antibody conjugate, including:

the humanized anti-NTSR1 antibody or the antigen-binding fragment thereof as disclosed herein; and a therapeutic agent conjugated with the humanized anti-NTSR1 antibody or the antigen-binding fragment thereof.

Examples of the therapeutic agent include, but are not limited to antimetabolites, alkylating agents, alkylating-like agents, DNA minor groove alkylating agents, anthracyclines, antibiotics, calicheamicins, antimitotic agents, topoisomerase inhibitors, HDAC inhibitor, proteasome inhibitors, and radioisotopes. In some embodiments of the present disclosure, the therapeutic agent is mertansine (DM1), monomethyl auristin E (MMAE), seco-DUBA, exactecan, deruxtecan or monomethyl auristatin F (MMAF).

The present disclosure further provides a vector encoding the humanized anti-NTSR1 antibody or the antigen-binding fragment thereof as disclosed herein.

The present disclosure provides a genetically engineered cell containing the vector as disclosed herein, or expressing the aforementioned humanized anti-NTSR1 antibody or the antigen-binding fragment thereof.

An Example of the genetically engineered cell includes, but is not limited to an immune cell. In some embodiment of the disclosure, the genetically engineered cell is a T cell.

The present disclosure also provide a method for manufacturing the humanized anti-NTSR1 antibody or the antigen-binding fragment thereof as disclosed herein, including:
(a) introducing into a host cell one or more polynucleotides encoding the humanized anti-NTSR1 antibody or the antigen-binding fragment thereof; (b) culturing the host cell under conditions favorable to expression of the one or more polynucleotides; and (c) optionally, isolating the humanized anti-NTSR1 antibody or the antigen-binding fragment thereof from the host cell and/or a medium in which the host cell is grown.

The present disclosure further provides a pharmaceutical composition, including: an effective amount of the humanized anti-NTSR1 antibody or the antigen-binding fragment thereof, the antibody conjugate, or the genetically engineered cell as disclosed herein; and a pharmaceutically acceptable carrier.

In some embodiments of the present disclosure, the pharmaceutical composition is provided for treating, prophylactic treating and/or preventing a disease and/or disorder caused by or related to NTSR1 activity and/or signaling in a subject in need of such treatment.

In some embodiments of the present disclosure, the disease is a cancer. Examples of the cancer include, but are not limited to a head and neck cancer, lung cancer, liver cancer, gastric cancer, pancreatic cancer, breast cancer, prostate cancer or colorectal cancer.

The present disclosure also provides a method for detecting NTSR1 in a sample, including contacting the sample with the humanized anti-NTSR1 antibody or the antigen-binding fragment thereof as disclosed herein.

The present disclosure further provides a kit for detecting NTSR1 in a sample, including the humanized anti-NTSR1 antibody or the antigen-binding fragment thereof as disclosed herein.

BRIEF DESCRIPTION OF DRAWINGS

FIG. 1A shows the sequence alignment between mouse $V_L$ (m7c3) and human template (4d5) (VKI). The first line shows the residue numbers according to the Kabat scheme. The mismatches are shown with underline. The Kabat CDRs are shown in square brackets.

FIG. 1B shows the sequence alignment between mouse $V_H$ (m7c3) and human template (4d5) (VHIII). The first line shows the residue numbers according to the Kabat scheme. The mismatches are shown with underline. The Kabat CDRs are shown in square brackets.

FIG. 2A shows the sequence alignment between mouse $V_L$ (m7c3) and human template (IMGT) (VKII). The first line shows the residue numbers according to the Kabat scheme. The mismatches are shown with underline. The Kabat CDRs are shown in square brackets.

FIG. 2B shows the sequence alignment between mouse $V_H$ (m7c3) and human template (IMGT) (VHI). The first line shows the residue numbers according to the Kabat scheme. The mismatches are shown with underline. The Kabat complementarity determining regions (CDRs) are shown in square brackets.

FIGS. 6A, 6B and 6C show the $V_H$ and $V_L$ sequence alignments between mouse 7C3, AKT2, and the humanized antibodies AKT2 HuHu and AKT2 HuHd with affinity maturation. The mutation process of the $V_H$ and $V_L$ of the humanized antibodies AKT2 HuHu and AKT2 HuHd were performed as described in Example 5.

DETAILED DESCRIPTION OF THE INVENTION

Figure 3A:
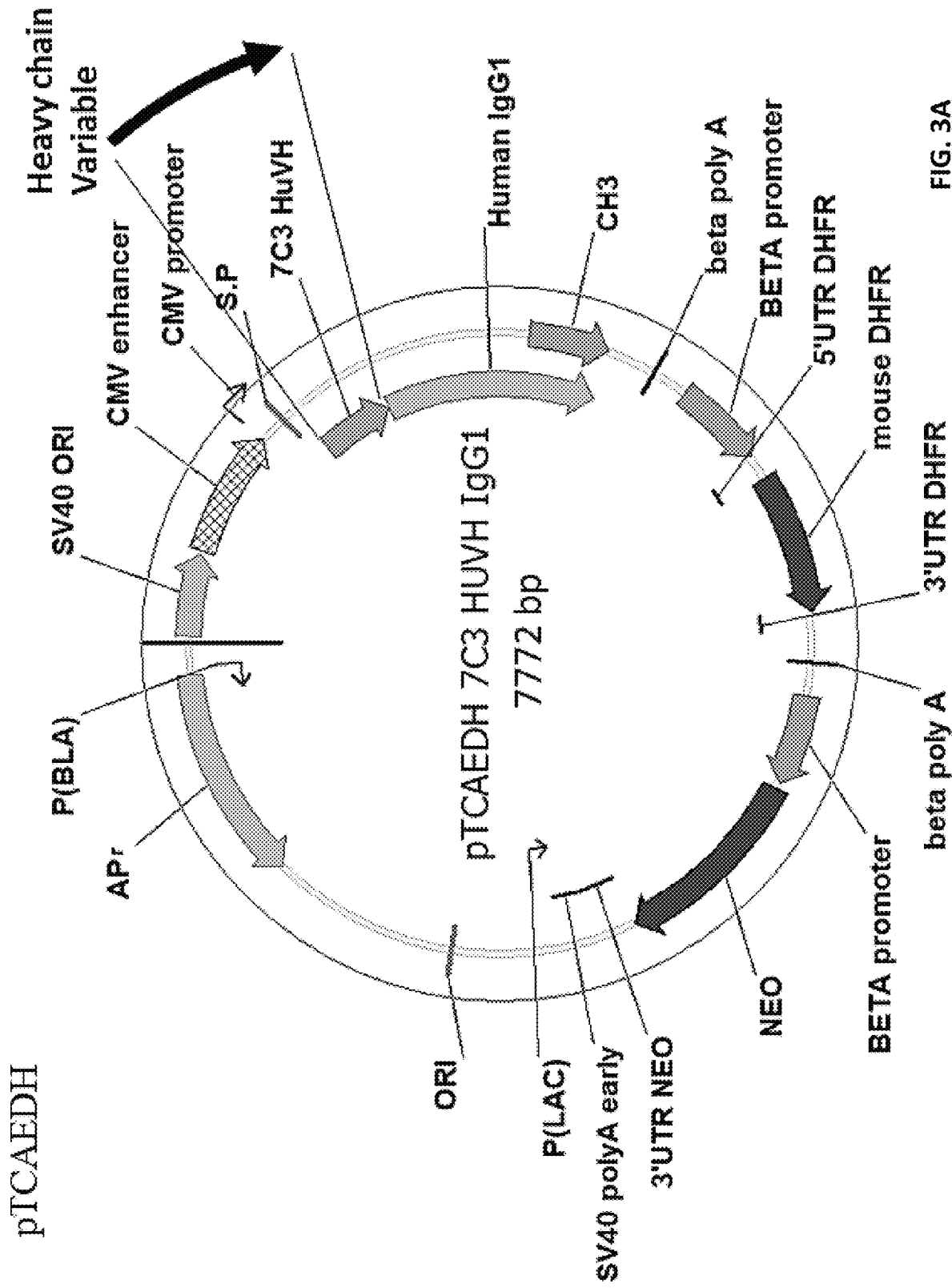
FIGS. 3A and 3B show expression vectors for generation of mouse-human chimera and humanized editions of anti-NTSR1 monoclonal antibody (mAb) as described in Example 2.

Unless otherwise defined, scientific and technical terms used herein shall have the meanings that are commonly understood by those of ordinary skill in the art. Furthermore, unless otherwise required by context, singular terms shall include pluralities and plural terms shall include the singular. Generally, nomenclatures used in connection with, and techniques of, cell and tissue culture, molecular biology, and protein and oligo- or polynucleotide chemistry and hybridization described herein are those well-known and commonly used in the art.

The practice of the present disclosure may employ technologies comprising conventional techniques of cell biology, cell culture, antibody technology, and genetic engineering, which are within the ordinary skills of the art. Such techniques are explained fully in the literature.

Standard techniques are used for recombinant DNA, oligonucleotide synthesis, and tissue culture and transformation (e.g., electroporation, lipofection). Enzymatic reactions and purification techniques are performed according to manufacturer's specifications or as commonly accomplished in the art or as described herein. The foregoing techniques and procedures are generally performed according to conventional methods well known in the art and as described in various general and more specific references that are cited and discussed throughout the present specification. See e.g., Sambrook et al., Molecular Cloning: A Laboratory Manual (3rd ed., Cold Spring Harbor Laboratory Press, Cold Spring Harbor, N.Y. (2001)), which is incorporated herein by reference. The nomenclatures utilized in connection with, and the laboratory procedures and techniques of, analytical chemistry, synthetic organic chemistry, and medicinal and pharmaceutical chemistry described herein are those well-known and commonly used in the art. Standard techniques are used for chemical syntheses, chemical analyses, pharmaceutical preparation, formulation, and delivery, and treatment of patients.

As utilized in accordance with the present disclosure, the following terms, unless otherwise indicated, shall be understood to have the following meanings: The term "and/or" as used herein is to be taken as specific disclosure of each of the two specified features or components with or without the other. For example "A and/or B" is to be taken as specific disclosure of each of (i) A, (ii) B and (iii) A and B, just as if each is set out individually herein.

It must be noted that, as used in this specification and the appended claims, the singular forms "a," "an," and "the" include plural referents unless the content clearly dictates otherwise.

The term "antibody", as used herein, means any antigen-binding molecule or molecular complex comprising at least one CDR that specifically binds to or interacts with a particular antigen (e.g., NTSR1). The term "antibody" includes immunoglobulin molecules comprising four polypeptide chains, two heavy (H) chains and two light (L) chains inter-connected by disulfide bonds, as well as multimers thereof (e.g., IgM). Each heavy chain comprises a $V_H$ and a heavy chain constant region. The heavy chain constant region comprises three domains, $C_{H1}$, $C_{H2}$ and $C_{H3}$. Each light chain comprises a $V_L$ and a light chain constant region. The light chain constant region comprises one domain ($C_{L1}$). The $V_H$ and $V_L$ can be further subdivided into regions of hypervariability, termed CDRs, interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. In different embodiments of the disclosure, the FRs of the anti-NTSR1 antibody (or antigen-binding portion thereof) may be identical to the human germline sequences, or may be naturally or artificially modified. An amino acid consensus sequence may be defined based on a side-by-side analysis of two or more CDRs.

As used herein, the term "being specific to" or "binding specifically to" means that an antibody does not cross react to a significant extent with other epitopes.

As used herein, the term "epitope" refers to the site on the antigen to which an antibody binds.

As used herein, the term "complementarity determining region (CDR)" refers to the non-contiguous antigen combining sites found within the variable region of both heavy and light chain polypeptides. CDRs have been described by Kabat et al., J. Biol. Chem. 252:6609-6616 (1977); Kabat et al., U.S. Dept. of Health and Human Services, "Sequences of proteins of immunological interest" (1991); by Chothia et al., J. Mol. Biol. 196:901-917 (1987); and MacCallum et al., J. Mol. Biol. 262:732-745 (1996), where the definitions include overlapping or subsets of amino acid residues when compared against each other.

The term "monoclonal antibody (mAb)" as used herein is not limited to antibodies produced through hybridoma technology. A monoclonal antibody is derived from a single clone, including any eukaryotic, prokaryotic, or phage clone, by any means available or known in the art.

The term "chimeric" antibody as used herein refers to an antibody having variable sequences derived from a non-human immunoglobulin and human immunoglobulin constant regions, typically chosen from a human immunoglobulin template.

"Humanized" forms of non-human antibodies are chimeric immunoglobulins that contain minimal sequences derived from non-human immunoglobulin. In general, a humanized antibody will comprise substantially all of at least one, and typically two, variable domains, in which all or substantially all of the CDR regions correspond to those of a non-human immunoglobulin and all or substantially all of the FR regions are those of a human immunoglobulin sequence.

As used herein, the term "nanobody" refers to an antibody comprising the small single variable domain (VHH of antibodies obtained from camelids and dromedaries. Antibody proteins obtained from members of the camel and dromedary (*Camelus baclrianus* and *Camelus dromaderius*) family including new world members such as llama species (*Lama paccos, Lama glama* and *Lama vicugna*) have been characterized with respect to size, structural complexity and antigenicity for human subjects. Certain IgG antibodies from this family of mammals as found in nature lack light chains, and are thus structurally distinct from the typical four chain quaternary structure having two heavy and two light chains, for antibodies from other animals.

The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex.

As used in the present disclosure, the term "therapeutic agent" means any compound, substance, drug, drug or active ingredient having a therapeutic or pharmacological effect that is suitable for administration to a mammal, for example a human.

As used herein, the term "immune cell" refers to cells that play a role in the immune response. Immune cells are of hematopoietic origin, and include lymphocytes, such as B cells and T cells; natural killer cells; myeloid cells, such as monocytes, macrophages, eosinophils, mast cells, basophils, and granulocytes.

As used herein, the term "T cell" includes $CD4^+$ T cells and $CD8^+$ T cells. The term T cell also includes T helper 1 type T cells, T helper 2 type T cells, T helper 17 type T cells and inhibitory T cells.

As used herein, the term "vector" is intended to refer to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The term "genetically engineered" or "genetic engineering" of cells means manipulating genes using genetic materials for the change of gene copies and/or gene expression level in the cell. The genetic materials can be in the form of DNA or RNA. The genetic materials can be transferred into cells by various means including viral transduction and non-viral transfection. After being genetically engineered, the expression level of certain genes in the cells can be altered permanently or temporarily.

As used in the present disclosure, the term "pharmaceutical composition" means a mixture containing therapeutics administered to a mammal, for example a human, for preventing, treating, or eliminating a particular disease or pathological condition that the mammal suffers.

As used herein, the term "therapeutically effective amount" or "effective amount" refers to the amount of an antibody that, when administered to a mammal or other subject for treating a disease, is sufficient to effect such treatment for the disease.

As used herein, the terms "treatment," "treating," and the like, covers any treatment of a disease in a mammal, particularly in a human, and includes: (a) preventing the disease from occurring in a subject which may be predisposed to the disease but has not yet been diagnosed as having it; (b) inhibiting the disease, i.e., arresting its development; and (c) relieving the disease, i.e., causing regression of the disease.

The term "preventing" or "prevention" is recognized in the art, and when used in relation to a condition, it includes administering, prior to onset of the condition, an agent to reduce the frequency or severity of or to delay the onset of symptoms of a medical condition in a subject, relative to a subject which does not receive the agent.

As interchangeably used herein, the terms "individual," "subject," "host," and "patient," refer to a mammal, including, but not limited to, murines (rats, mice), non-human primates, humans, canines, felines, ungulates (e.g., equines, bovines, ovines, porcines, caprines), etc.

As used herein, the term "in need of treatment" refers to a judgment made by a caregiver (e.g. physician, nurse, nurse practitioner, or individual in the case of humans; veterinarian in the case of animals, including non-human mammals) that a subject requires or will benefit from treatment. This judgment is made based on a variety of factors that are in the realm of a care giver's expertise, but that includes the knowledge that the subject is ill, or will be ill, as the result of a condition that is treatable by the compounds of the present disclosure.

"Cancer," "tumor," and like terms include precancerous, neoplastic, transformed, and cancerous cells, and can refer to a solid tumor, or a non-solid cancer (see, e.g., Edge et al. AJCC Cancer Staging Manual (7th ed. 2009); Cibas and Ducatman Cytology: Diagnostic principles and clinical correlates (3rd ed. 2009)). Cancer includes both benign and malignant neoplasms (abnormal growth). "Transformation" refers to spontaneous or induced phenotypic changes, e.g., immortalization of cells, morphological changes, aberrant cell growth, reduced contact inhibition and anchorage, and/or malignancy (see, Freshney, Culture of Animal Cells a Manual of Basic Technique (3rd ed. 1994)). Although transformation can arise from infection with a transforming virus and incorporation of new genomic DNA, or uptake of exogenous DNA, it can also arise spontaneously or following exposure to a carcinogen.

As used herein, the term "sample" encompasses a variety of sample types obtained from an individual, subject or patient and can be used in a diagnostic or monitoring assay. The definition encompasses blood and other liquid samples of biological origin, solid tissue samples such as a biopsy specimen or tissue cultures or cells derived therefrom and the progeny thereof.

The present disclosure provides a humanized antibody that is specific to and has high affinities for human NTSR1. The anti-NTSR1 antibody or an antigen-binding fragment thereof can deliver therapeutic benefits to a subject. The anti-NTSR1 antibody or the antigen-binding fragment thereof according to the disclosure can be used as therapeutics for treating and/or diagnosing a variety of disorders mediated by NTSR1, which are more fully described herein.

The antibody or the antigen-binding fragment thereof according to embodiments of the disclosure can be full-length (for example, having a heavy chain constant region selected from the group consisting of IgGl, IgG2 and IgG4 isoforms, and a light chain constant region selected from the group consisting of κ and λ isotypes), or may comprise only an antigen-binding portion (for example, a Fab, F(ab')$_2$, or scFv fragment), and may be modified to affect functionalities as needed.

Non-limiting examples of an antigen-binding fragment includes: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g. monovalent nanobodies, bivalent nanobodies, etc.), small modular immunopharmaceuticals (SMIPs), and shark variable IgNAR domains, are also encompassed within the expression "antigen-binding fragment," as used herein.

An antigen-binding fragment of an antibody typically comprises at least one variable domain. The variable domain may be of any size or amino acid composition and will generally comprise at least one CDR, which is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$-$V_H$, $V_H V_L$ or $V_L$-$V_L$ dimers. Alternatively, the antigen-binding fragment of an antibody may contain a monomeric $V_H$ or $V_L$ domain.

As with a full antibody molecule, an antigen-binding fragment may be monospecific or multi-specific (e.g., bispecific). A multi-specific antigen-binding fragment of an antibody will typically comprise at least two different variable domains, wherein each variable domain is capable of specifically binding to a separate antigen or to a different epitope on the same antigen. Any multi-specific antibody format, including the exemplary bispecific antibody formats disclosed herein, may be adapted for use in the context of an antigen-binding fragment of an antibody of the present invention using routine techniques available in the art.

In some embodiments of the present disclosure, the humanized anti-NTSR1 antibody or the antigen-binding fragment thereof includes a heavy chain variable region including the sequence of SEQ ID NO: 16, 11 or 13, or a sequence with at least about 90%, 91%, 92%, 93%, 94%, 95%, 96%, 97%, 98%, or 99% identity to the sequence of SEQ ID NO: 16, 11 or 13; and a light chain variable region ($V_L$) including the sequence of SEQ ID NO: 17, 15, 12 or 14, or a sequence with at least about 90%, 91%, 92%, 93%, 94%, 95%, 96%, 97%, 98%, or 99% identity to the sequence of SEQ ID NO: 17, 15, 12 or 14.

The term "sequence identity" means that two polynucleotide or amino acid sequences are identical (i.e., on a nucleotide-by-nucleotide or residue-by-residue basis) over the comparison window. The term "percentage of sequence identity" is calculated by comparing two optimally aligned sequences over the window of comparison, determining the number of positions at which the identical nucleic acid base (e.g., A, T, C, G, U, or 1) or amino acid residue occurs in both sequences to yield the number of matched positions, dividing the number of matched positions by the total number of positions in the comparison window (i.e., the window size), and multiplying the result by 100 to yield the percentage of sequence identity.

In some embodiments of the present disclosure, the humanized anti-NTSR1 antibody or the antigen-binding fragment thereof includes the $V_H$ including the sequence of SEQ ID NO: 16; and the $V_L$ including the sequence of SEQ ID NO: 17 or 15.

In some embodiments of the present disclosure, the humanized anti-NTSR1 antibody or the antigen-binding fragment thereof includes the $V_H$ including the sequence of SEQ ID NO: 13, and the $V_L$ including the sequence of SEQ ID NO: 12 or 14.

In some embodiments of the present disclosure, the humanized anti-NTSR1 antibody or the antigen-binding fragment thereof includes the $V_H$ including the sequence of SEQ ID NO: 11, and the $V_L$ including the sequence of SEQ ID NO: 12 or 14.

The humanized anti-NTSR1 antibody disclosed herein may comprise one or more amino acid substitutions, insertions and/or deletions in the framework and/or CDR regions of the heavy and light chain variable domains as compared to the corresponding germline sequences from which the antibodies were derived. Such mutations can be readily ascertained by comparing the amino acid sequences disclosed herein to germline sequences available from, for example, public antibody sequence databases. The present disclosure includes an antibody, and an antigen-binding fragment thereof, which are derived from any of the amino acid sequences disclosed herein, wherein one or more amino acids within one or more framework and/or CDR regions are mutated to the corresponding residue(s) of the germline sequence from which the antibody was derived, or to the corresponding residue(s) of another mammalian germline sequence, or to a conservative amino acid substitution of the corresponding germline residue(s) (such sequence changes are referred to herein collectively as "germline mutations"). A person of ordinary skill in the art, starting with the heavy and light chain variable region sequences disclosed herein, can easily produce numerous antibodies and antigen-binding fragments which comprise one or more individual germline mutations or combinations thereof. In certain embodiments, all of the framework and/or CDR residues within the $V_H$ and/or $V_L$ domains are mutated back to the residues found in the original germline sequence from which the antibody was derived. In other embodiments, only certain residues are mutated back to the original germline sequence, e.g., only the mutated residues found within the first 8 amino acids of FR1 or within the last 8 amino acids of FR4, or only the mutated residues found within CDR1, CDR2 or CDR3. In other embodiments, one or more of the framework and/or CDR residue(s) are mutated to the corresponding residue(s) of a different germline sequence (i.e., a germline sequence that is different from the germline sequence from which the antibody was originally derived). Furthermore, the antibodies of the present disclosure may contain any combination of two or more germline mutations within the framework and/or CDR regions, e.g., wherein certain individual residues are mutated to the corresponding residue of a particular germline sequence while certain other residues that differ from the original germline sequence are maintained or are mutated to the corresponding residue of a different germline sequence. Once obtained, antibodies and antigen-binding fragments that contain one or more germline mutations can be easily tested for one or more desired property such as, improved binding specificity, increased binding affinity, improved or enhanced antagonistic or agonistic biological properties (as the case may be), reduced immunogenicity, etc. Antibodies and antigen-binding fragments obtained in this general manner are encompassed within the present disclosure.

The antibodies of the present disclosure may be mono-specific, bi-specific, or multispecific. Multispecific antibodies may be specific for different epitopes of one target polypeptide or may contain antigen-binding domains specific for more than one target polypeptide. The anti-NTSR1 antibodies of the present disclosure can be linked to or co-expressed with another functional molecule, e.g., another peptide or protein. For example, an antibody or fragment thereof can be functionally linked (e.g., by chemical coupling, genetic fusion, noncovalent association or otherwise) to one or more other molecular entities, such as another antibody or antibody fragment to produce a bi-specific or a multispecific antibody with a second binding specificity. For example, the present disclosure includes bi-specific antibodies wherein one arm of an immunoglobulin is specific for NTSR1 or a fragment thereof, and the other arm of the immunoglobulin is specific for a second target or is conjugated to a therapeutic agent.

In some embodiments of the disclosure, the antibody or antigen-binding fragment thereof is in a form of chimeric antigen receptor.

In some embodiments of the present disclosure, the humanized anti-NTSR1 antibody or the antigen-binding fragment thereof may be used as antibody-drug conjugates (ADCs), which can specifically target NTSR1. That is, the present disclosure also provides an antibody conjugate, including the aforementioned humanized anti-NTSR1 antibody or the antigen-binding fragment, and therapeutic agent conjugated with the humanized anti-NTSR1 antibody or the antigen-binding fragment thereof. The therapeutic agent or payload can be any that are commonly used in ADCs. In some embodiments, the therapeutic agent or payload is selected from the group consisting of antimetabolites, alkylating agents, alkylating-like agents, DNA minor groove alkylating agents, anthracyclines, antibiotics, calicheamicins, antimitotic agents, topoisomerase inhibitors, HDAC inhibitor, proteasome inhibitors, and radioisotopes. For example, the therapeutic agents or payloads may include mertansine (DM1), monomethyl auristin E (MMAE), seco-DUBA, exactecan, deruxtecan or monomethyl auristatin F (MMAF). The methods for conjugation can be those known in the art.

The humanized anti-NTSR1 antibody or the antigen-binding fragment thereof may be encoded in a vector. The present disclosure also provide a vector encoding the humanized anti-NTSR1 antibody or the antigen-binding fragment thereof as described herein. In one embodiment, one type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

In another aspect, the present disclosure provides a genetically engineered cell expressing the humanized anti-NTSR1 antibody or the antigen-binding fragment thereof as described herein or containing the vector as described herein. The genetically engineered cell may be an immune cell, such as a T cell. In one embodiment of the disclosure, the antibody or antigen-binding fragment thereof is expressed on the surface of a cell. Particularly, the cell is a T-cell.

In some embodiments of the disclosure, the antibody or antigen-binding fragment thereof is in a form of chimeric antigen receptor.

The term "chimeric antigen receptor" or alternatively a "CAR" refers to a recombinant polypeptide construct comprising at least an extracellular antigen binding domain, a transmembrane domain and a cytoplasmic signaling domain (also referred to herein as "an intracellular signaling domain") comprising a functional signaling domain derived from a stimulatory molecule as defined below. In some embodiments, the domains in the CAR polypeptide construct are in the same polypeptide chain, e.g., comprise a chimeric fusion protein. In some embodiments, the domains in the CAR polypeptide construct are not contiguous with each other, e.g., are in different polypeptide chains.

An example of a method for manufacturing the humanized anti-NTSR1 antibody or the antigen-binding fragment thereof includes: (a) introducing into a host cell one or more polynucleotides encoding said antibody or antigen-binding fragment; (b) culturing the host cell under conditions favorable to expression of the one or more polynucleotides; and (c) optionally, isolating the antibody or the antigen-binding fragment from the host cell and/or a medium in which the host cell is grown.

The disclosure further provides pharmaceutical compositions including the humanized anti-NTSR1 antibody or antigen-binding fragment thereof, the antibody conjugate or the genetically engineered cell as described herein. The pharmaceutical compositions as described herein e are formulated with suitable diluents, carriers, excipients, and other agents that provide improved transfer, delivery, tolerance, and the like. The compositions may be formulated for specific uses, such as for veterinary uses or pharmaceutical uses in humans. The form of the composition and the excipients, diluents and/or carriers used will depend upon the intended uses of the antibody and, for therapeutic uses, the mode of administration. A multitude of appropriate formulations can be found in the formulary known to all pharmaceutical chemists: Remington's Pharmaceutical Sciences, Mack Publishing Company, Easton, Pa. These formulations include, for example, powders, pastes, ointments, jellies, waxes, oils, lipids, lipid (cationic or anionic) containing vesicles (such as LIPOFECTIN™, Life Technologies, Carlsbad, Calif.), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also Powell et al. "Compendium of excipients for parenteral formulations" PDA (1998) J Pharm Sci Technol 52:238-311.

The dose of antibody administered to a patient may vary depending upon the age and the size of the patient, target disease, conditions, route of administration, and the like. The preferred dose is typically calculated according to body weight or body surface area. When an antibody of the present disclosure is used for treating a condition or disease associated with NTSR1 in an adult patient, it may be advantageous to intravenously administer the antibody of the present disclosure. Depending on the severity of the condition, the frequency and the duration of the treatment can be adjusted. Effective dosages and schedules for administering the antibody may be determined empirically; for example, patient progress can be monitored by periodic assessment, and the dose adjusted accordingly. Moreover, interspecies scaling of dosages can be performed using well-known methods in the art (e.g., Mordenti et al., 1991, Pharmaceut. Res. 8:1351).

Various delivery systems are known and can be used to administer the pharmaceutical composition of the disclosure, e.g., encapsulation in liposomes, microparticles, microcapsules, recombinant cells capable of expressing the mutant viruses, receptor mediated endocytosis (see, e.g., Wu et al., 1987, J. Biol. Chem. 262:4429-4432). Methods of introduction include, but are not limited to, intradermal, intramuscular, intraperitoneal, intravenous, subcutaneous, intranasal, epidural, and oral routes. The composition may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local.

The pharmaceutical composition of the present disclosure can be delivered subcutaneously or intravenously with a standard needle and syringe. In addition, with respect to subcutaneous delivery, a pen delivery device readily has applications in delivering a pharmaceutical composition of the present disclosure. Such a pen delivery device can be reusable or disposable. A reusable pen delivery device generally utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded.

In certain situations, the pharmaceutical composition can be delivered in a controlled release system. In one embodiment, a pump may be used (see Langer, supra; Sefton, 1987, CRC Crit. Ref. Biomed. Eng. 14:201). In another embodiment, polymeric materials can be used; see, Medical Applications of Controlled Release, Langer and Wise (eds.), 1974, CRC Pres., Boca Raton, Fla. In yet another embodiment, a controlled release system can be placed in proximity of the composition's target, thus requiring only a fraction of the systemic dose (see, e.g., Goodson, 1984, in Medical Applications of Controlled Release, supra, vol. 2, pp. 115-138). Other controlled release systems are discussed in the review by Langer, 1990, Science 249:1527-1533.

The injectable preparations may include dosage forms for intravenous, subcutaneous, intracutaneous and intramuscular injections, drip infusions, etc. These injectable preparations may be prepared by methods publicly known. For example, the injectable preparations may be prepared, e.g., by dissolving, suspending or emulsifying the antibody or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared is preferably filled in an appropriate ampoule.

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc.

In some embodiments of the disclosure, the pharmaceutical composition is for use in treating, prophylactic treating and/or preventing a disease and/or disorder caused by or related to NTSR1 activity and/or signaling. Alternatively, the present disclosure also provides a method for treating, prophylactic treating and/or preventing a disease and/or disorder caused by or related to NTSR1 activity and/or signaling in a subject in need of such treatment, comprising administering to the subject the pharmaceutical composition. In some embodiments, the disease is a cancer, such as head and neck cancer, lung cancer, liver cancer, gastric cancer, pancreatic cancer, breast cancer, prostate cancer or colorectal cancer.

The present disclosure further provides a method for detecting NTSR1 in a sample, which includes contacting a sample with the anti-NTSR1 antibody or the antigen-binding fragment thereof as described herein. The present disclosure also provides a kit for detecting NTSR1 in a sample, including the humanized anti-NTSR1 antibody or the antigen-binding fragment thereof.

The humanized anti-NTSR1 antibody or the antigen-binding fragment thereof as described herein may also be used to detect and/or measure NTSR1, or NTSR1-expressing cells in a sample, e.g., for diagnostic purposes. For example, an anti-NTSR1 antibody, or the antigen binding fragment thereof, may be used to diagnose a condition or disease characterized by aberrant expression (e.g., over-expression, under-expression, lack of expression, etc.) of NTSR1. Exemplary diagnostic assays for NTSR1 may comprise, e.g., contacting a sample, obtained from a patient, with an anti-NTSR1 antibody of the disclosure, wherein the anti-NTSR1 antibody is labeled with a detectable label or reporter molecule. Alternatively, an unlabeled anti-NTSR1 antibody can be used in diagnostic applications in combination with a secondary antibody which is itself detectably labeled. The detectable label or reporter molecule can be a radioisotope, such as $^3H$, $^{14}C$, $^{32}P$, $^{35}S$, or $^{125}I$; a fluorescent or chemiluminescent moiety such as fluorescein isothiocyanate, or rhodamine; or an enzyme such as alkaline phosphatase, beta-galactosidase, horseradish peroxidase, or luciferase. Specific exemplary assays that can be used to detect or measure NTSR1 in a sample include enzyme-linked immunosorbent assay (ELISA), radioimmunoassay (RIA), and fluorescence-activated cell sorting (FACS).

The following examples are provided to aid those skilled in the art in practicing the present disclosure.

EXAMPLES

The following examples illustrate the development and use of NTSR1-specific antibodies to suppress tumor growth by inducing an anti-NTSR1 immune response.

Example 1

Humanization of Anti-NTSR1 mAb 7C3
Selection of Human V Region Framework Sequences:
Mouse mAb 7C3 may induce potent immunogenicity and anti-drug antibody in patients. Therefore, humanization of 7C3 is an essential and critical step for further drug development. The mouse monoclonal antibody 7C3 (also referred as m7C3) comprising the $V_H$ and $V_L$ of SEQ ID NOs:7 and 8 was used as the parent antibody, and the 7C3 mAb CDR sequences as shown in SEQ ID NOs: 1 to 6 based on the Kabat definitions are shown in FIGS. 1A, 11B, 2A and 2B.

TABLE 1

Lists of amino acid sequence

| | Sequence | SEQ ID NO. |
|---|---|---|
| CDRH1 of m7C3 | GYTFTSSWIH | 1 |
| CDRH2 of m7C3 | QIRPNSGNTYYNEKFKV | 2 |
| CDRH3 of m7C3 | YYYGFDY | 3 |
| CDRL1 of m7C3 | RSSQSIVHSNGNTYLE | 4 |

TABLE 1-continued

Lists of amino acid sequence

| | Sequence | SEQ ID NO. |
|---|---|---|
| CDRL2 of m7C3 | KVSNRFS | 5 |
| CDRL3 of m7C3 | FQGSHLPWT | 6 |
| MOUSE 7C3 $V_H$ (m7C3 $V_H$) | QVQLQQPGSVLVRPGDSVMLSCKASGYTFTSSWIHWAKQRPGQGPEWIGQIRPN SGNTYYNEKFKVKATLTVDTSSSTAYVDLSSLTSEDSAVYYCARYYYGFDYWGQ GTTVTVSS | 7 |
| MOUSE 7C3 $V_L$ (m7C3 $V_L$) | DVLMTQTPLSLPVSLGDQASISCRSSQSIVHSNGNTYLEWYLQKPGQSPKLLIYKV SNRFSGVPDRFSGSGSGTDFTLKISRVEAEDLGVYYCFQGSHLPWTFGGGTKLEI K | 8 |
| MOUSE AKT2 $V_H$ (AKT2 $V_H$) | QVQLQQPGSVLVRPGASVKLSCKASGYAFTSSWIHWAKQRPGQGLEWIGQIRP NSGNTYYNEKFKVKATLTVDTSSSTAYVDLSSLTSEDSAVYYCARYHYGFDYWGQ GTLVTVSS | 9 |
| MOUSE AKT2 $V_L$ (AKT2 $V_L$) | DVLMTQTPLSLPVSLGDQASISCRSSQSIVHSNGNTYLEWYLQKPGQSPKLLIYKV SNRFSGVPDRFSGSGSGTDFTLKISRVEAEDLGVYYCFQGAHLPWTFGGGTKLEI K | 10 |
| 7C3 Hd$V_H$ | EVQLVESGGGLVQPGGSLRLSCAASGYTFTSSWIHWVRQAPGKGLEWVAQIRP NSGNTYYNEKFKVRFTISRDDSKNTLYLQMNSLRAEDTAVYYCARYYYGFDYWG QGTLVTVSS | 11 |
| 7C3 Hd$V_L$ | DIQMTQSPSSLSASVGDRVTITCRSSQSIVHSNGNTYLEWYQQKPGKAPKLLIYK VSNRFSGVPSRFSGSGSGTDFTLTISSLQPEDFATYYCFQGSHLPWTFGQGTKVEI K | 12 |
| 7C3 Hu$V_H$ | QVQLVQSGAEVKKPGASVKVSCKASGYTFTSSWIHWVRQAPGQGLEWMGQIR PNSGNTYYNEKFKVRVTMTRDTSTSTVYMELSSLRSEDTAVYYCARYYYGFDYW GQGTLVTVSS | 13 |
| 7C3 Hu$V_L$ | DIVMTQTPLSLSVTPGQPASISCRSSQSIVHSNGNTYLEWYLQKPGQSPQLLIYKV SNRFSGVPDRFSGSGSGTDFTLKISRVEAEDVGVYYCFQGSHLPWTFGQGTKVEI K | 14 |
| AKT2 Hd$V_L$ | DIQMTQSPSSLSASVGDRVTITCRSSQSIVHSNGNTYLEWYQQKPGKAPKLLIYK VSNRFSGVPSRFSGSGSGTDFTLTISSLQPEDFATYYCFQGAHLPWTFGQGTKVEI K | 15 |
| AKT2 Hu$V_H$ | QVQLVQSGAEVKKPGASVKVSCKASGYAFTSSWIHWVRQAPGQGLEWMGQIRP NSGNTYYNEKFKVRVTMTRDTSTSTVYMELSSLRSEDTAVYYCARYHYGFDYW GQGTLVTVSS | 16 |
| AKT2 Hu$V_L$ | DIVMTQTPLSLSVTPGQPASISCRSSQSIVHSNGNTYLEWYLQKPGQSPQLLIYKV SNRFSGVPDRFSGSGSGTDFTLKISRVEAEDVGVYYCFQGAHLPWTFGQGTKVEI K | 17 |
| HUCDRH1 | GYAFTSSWIH | 18 |
| HUCDRH2 | QIRPNSGNTYYNEKFKV | 19 |
| HUCDRH3 | YHYGFDY | 20 |
| HUCDRL1 | RSSQSIVHSNGNTYLE | 21 |
| HUCDRL2 | KVSNRFS | 22 |
| HUCDRL3 | FQGAHLPWT | 23 |
| Human IGKV1 | DIQMTQSPSSLSASVGDRVTITCRASQDVNTAVAWYQQKPGKAPKLLIYSASFL ESGVPSRFSGSGSGTDFTLTISSLQPEDFATYYCQQHYTTPPTFGQGTKVEIKR | 24 |
| Human IGHV3 | EVQLVESGGGLVQPGGSLRLSCAASGFTFSDTYIHWVRQAPGKGLEWVARIYPT NGYTRYADSVKGRFTISRDDSKNTLYLQMNSLRAEDTAVYYCARWGGDGFYAM DVWGQGTLVTVSS | 25 |
| Human IGVK2 | DIVMTQTPLSLSVTPGQPASISCKSSQSLLHSDGKTYLYWYLQKPGQSPQLLI YEVSSRFSGVPDRFSGSGSGTDFTLKISRVEAEDVGVYYCQQYSGYPLTFGQG TKVEIKR | 26 |

TABLE 1-continued

Lists of amino acid sequence

| Sequence | | SEQ ID NO. |
|---|---|---|
| Human IGHV1 | QVQLVQSGAEVKKPGASVKVSCKASGYTFTGYYMHWVRQAPGQGLEWMGIINP SGGSTSYAQKFQGRVTMTRDTSTSTVYMELSSLRSEDTAVYYCARWGGDGFY AMDVWGQGTLVTVSS | 27 |

For humanized 7C3 4D5 (7C3 HdHd) preparation, a human acceptor framework 41D5 was selected from a framework that has been validated in the clinical trial study. Human heavy and light chain framework sequences in the $V_H$ subgroup III (IGHV3, SEQ ID NO: 25) and $V_L$ K subgroup I (IGKV1, SEQ ID NO: 24) have been validated in the clinic and also been used in many humanized antibodies with success.

As shown in FIG. 1A, the framework sequences of IGKV1 $V_L$ differ from those in the mouse mAb 7C3 by 25 amino acids (the underlined residues), which corresponds to a 30.86% (25/81 total residues in the framework regions) variation. In addition, in FIG. 11B, the framework sequences of IGHV3 $V_H$ differs from those in the mouse mAb 7C3 by 35 amino acids (the underlined residues), which corresponds to a 42.68% (35/82 total residues in the framework regions) variation. The $V_H$ and $V_L$ of the humanized 7C3 4D5 (7C3 HdHd) are shown in Table 1, SEQ ID NO: 11 (7C3 HdV$_H$) and SEQ ID NO: 12 (7C3 HdV$_L$).

For humanized 7C3 IMGT (7C3 HuHu) preparation, human germ-line $V_L$ and $V_H$ sequences with the highest degree of homology with the mouse mAb 7C3 framework regions were identified from the IMGT database (the International Immunogenetics Information System®). The homology searches may be performed with BLAST or similar methods. The mouse mAb 7C3 variable region sequences were used as query sequences. These searches identified the human germline gene IGHV1 ($V_H$, SEQ ID NO: 27) and IGVK2 ($V_L$, SEQ ID NO: 26), respectively, as the $V_H$ and $V_L$ sequences most homologous to the corresponding heavy chain and light chain framework sequences in the mouse mAb 7C3.

As shown in FIG. 2A, the framework sequences of IGVK2 $V_L$ differ from those in the mouse mAb 7C3 by 11 amino acids (the underlined residues), which corresponds to a 13.58% (11/81 total residues in the framework regions) variation. As shown in FIG. 2B, the framework sequences of IGHV1 $V_H$ differ from those in the mouse mAb 7C3 by 26 amino acids (the underlined residues), which corresponds to a 31.70% (26/82 total residues in the framework regions) variation. The $V_H$ and $V_L$ of the humanized 7C3 IMGT (7C3 HuHu) are shown in Table 1, SEQ ID NO:13 (7C3 HuV$_H$) and SEQ ID NO:14 (7C3 HuV$_L$)

These two pairs of light chain and heavy chain sequences (humanized 7C3 4D5 and humanized 7C3 IMGT) are used as examples for the construction of humanized antibodies against human NTSR1.

Example 2

Expression of Full Length Antibodies

Figure 3B:
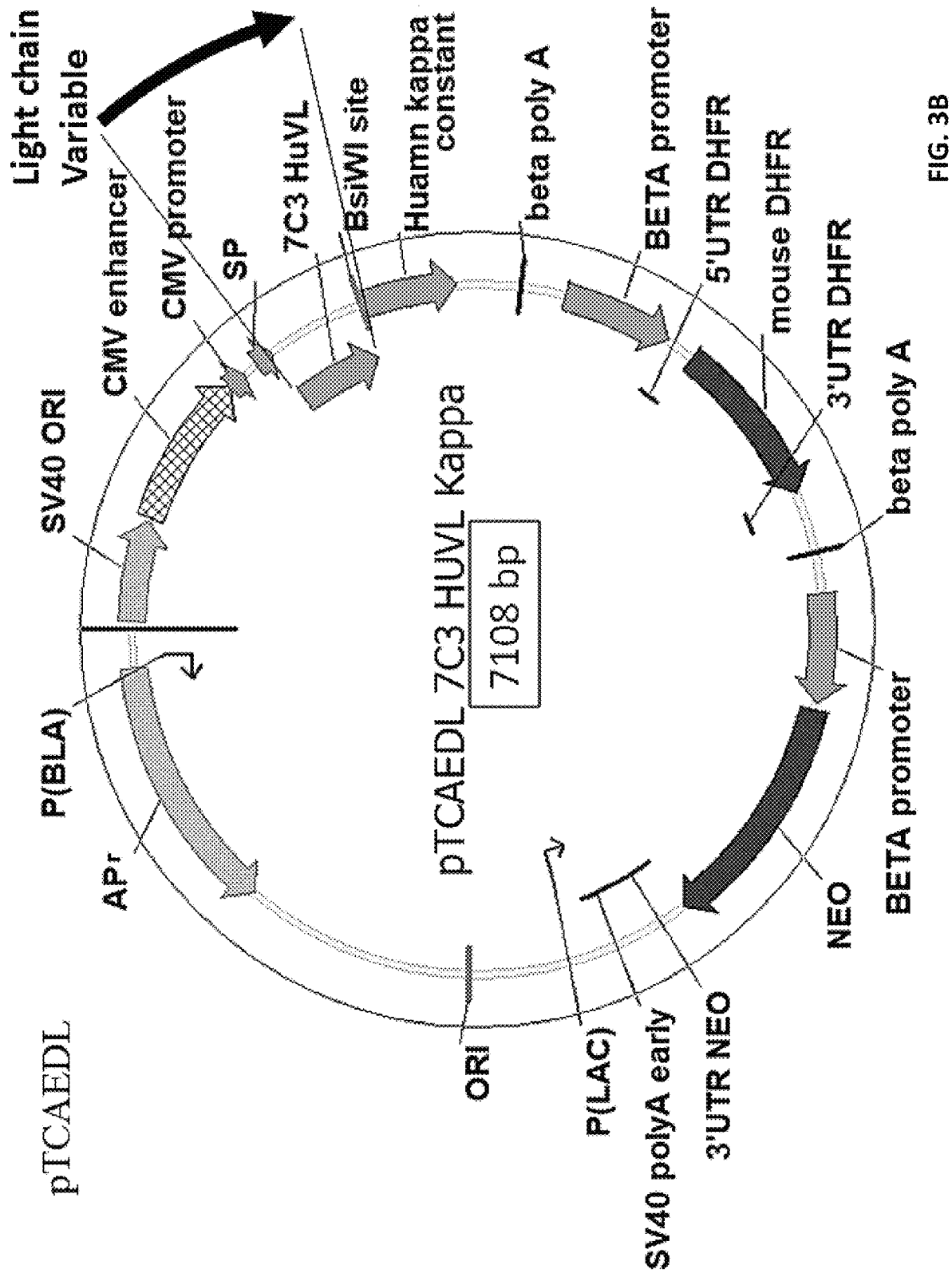

In order to confirm the affinity change of mouse antibodies after humanization, the DNA segments encoding the $V_H$ and $V_L$ of humanized 7C3 4D5 and humanized 7C3 IMGT were directly generated by the nucleotide synthesis method, respectively. The DNA segments encoding the $V_H$ and $V_L$ of mouse 7C3, humanized 7C3 4D5 and humanized 7C3 IMGT (Tables 1 and 2) were sub-cloned into a set of human Fc chimera antibody expression vector pTCAEDH and pTCAEDL, as shown in FIGS. 3A and 3B. Plasmids pTCAEDH 7C3 HUVH IgG1 and pTCAEDL 7C3 HUVL Kappa were introduced into host cells to prepare recombinant antibody-expressing cells. As the host cells for antibody expression, the FREESTYLE™ 293 cells (manufactured by INVITROGEN®) were used.

TABLE 2

| Clone name and $V_H/V_L$ composition | |
|---|---|
| Clone Name | $V_H$, $V_L$ |
| 7C3 MM (m7C3) | m7C3 $V_H$, m7C3 $V_L$ |
| 7C3 HuHu | 7C3 HuV$_H$, 7C3 HuV$_L$ |
| 7C3 HdHd | 7C3 HuV$_H$, 7C3 HuV$_L$ |
| 7C3 HuHd | 7C3 HuV$_H$, 7C3 HuV$_L$ |
| 7C3 HdHu | 7C3 HuV$_H$, 7C3 HuV$_L$ |
| AKT2 | AKT2 $V_H$, AKT2 $V_L$ |
| AKT2 HuHd | AKT2 HuV$_H$, AKT2 HdV$_L$ |
| AKT2 HuHu | AKT2 HuV$_H$, AKT2 HuV$_L$ |

The following procedures are used to transfect the vector thus constructed into suspensions of FREESTYLE™ 293 cells in a 30 ml volume. FREESTYLE™ 293 cells were passed at $2×10^6$ cells/ml for 15 ml of FREESTYLE™ 293 Expression Medium in culture flask. The flask(s) was placed in an incubator at 37° C. containing 8% $CO_2$ and shake at 135 rpm. Then, 37.5 µg of plasmid DNA was diluted into 1.5 ml sterile 150 mM NaCl to a total volume of 1.5 ml. In a separate tube, 37.5 µl of PEI (2.0 mg/ml) was diluted in 1.5 ml sterile 150 mM NaCl. The DNA and PEI solutions were allowed to sit at room temperature for 5 minutes. The solutions were mixed gently by inverting the tubes and then allowed the tubes to stand at room temperature for around 10-20 minutes. DNA-PEI mixture was added into FREESTYLE™ 293 cells and incubated the transfected cell on an orbital shaker platform rotating at 135-150 rpm at 37° C., 8% $CO_2$ in an incubator for 4 hours. Then, an equal volume of fresh culture medium was added to a total volume of 30 ml, and the cells were cultured for 5-7 days. Cells are then harvested for antibody purification and quantification.

The collected supernatant was filtered through 0.2 µm filters (manufactured by MILLIPORE®) to remove particulate after cultivation. The culture supernatant containing the antibody was affinity-purified using Protein A (manufactured by MILLIPORE®), 1.5 M Glycine/NaOH buffer, 3 M NaCl (pH 9.0), as an absorption buffer, and 0.2 M Glycine/ HCl buffer (pH 2.5) as an elution buffer. The elution fractions were adjusted to around pH 6.0-7.0 by adding 1 M Tris/HCl buffer (pH 9.0). The prepared antibody solution was replaced with PBS using a dialysis membrane (10,000 MW cut, manufactured by SPECTRUM LABORATO- RIES®) and filter-sterilized through a membrane filter (manufactured by MILLPORE®) having a pore size of 0.22 m to yield the purified antibody. The concentration of the purified antibody was determined by measuring the absorbance at 280 nm and converting the measured value based on 1.45 optimal density equaling 1 mg/ml.

Example 3

Determination of Binding Affinity of the Humanized Antibodies by ELISA

ELISA plates were coated with 1-2 μg/100 μL per well of NTSR1 linear L2-biotin protein. Wells were rinsed for 3 times with PBS and blocked with 300 μL of 5% MPBS per well for 2 hr at 37° C. After washing with PBS, wells were incubated with serial diluted NTSR1 antibodies in 5% MPBS for 1.5 hours at 37° C. The plates were washed and goat polyclonal anti-human IgG-HRP antibody (1:10,000) (JACKSON IMMUNORESEARCH®) was added into each well. The OD at 650 nm and at 450 nm was read. Readings were obtained by subtracting $OD_{650}$ from $OD_{450}$ and the binding affinities of antibodies were calculated by non-linear regression with Prism software (GRAPHPAD®).

Figure 4:
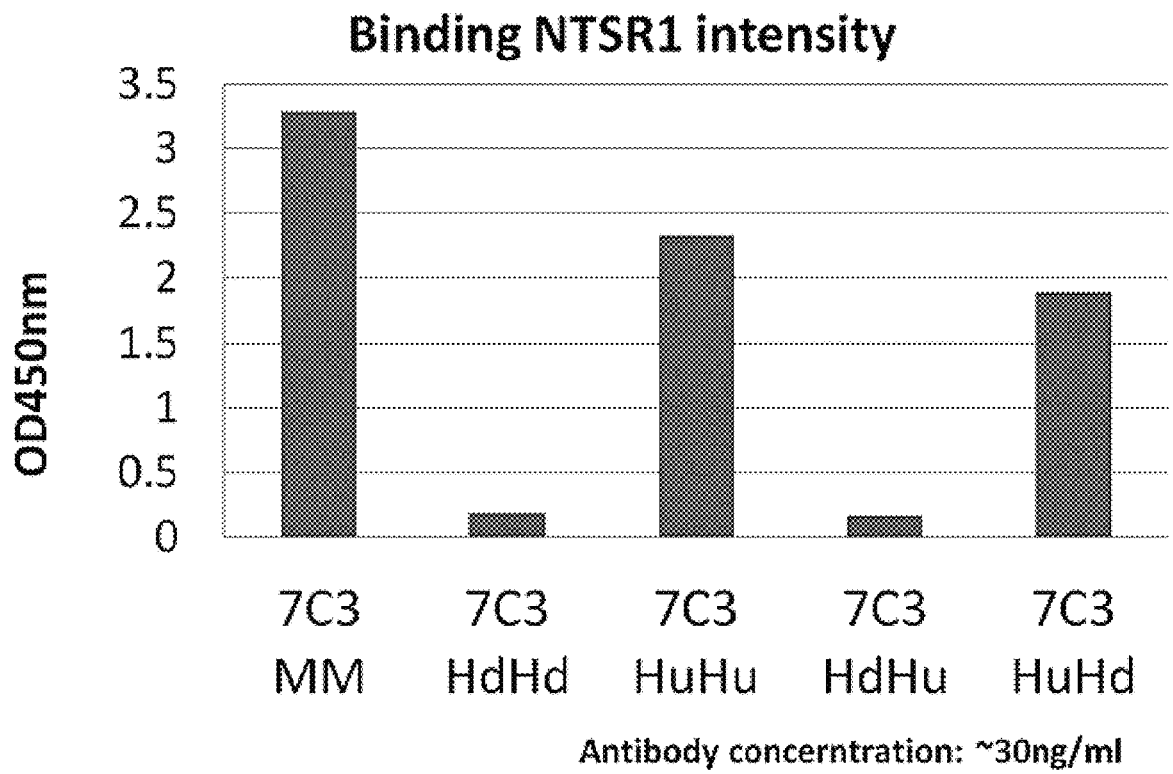
FIG. 4 depicts results of binding affinity analysis of the mouse-human chimera antibody 7C3 MM, the humanized antibodies 7C3 HdHd, 7C3 HuHu, 7C3 HdHu and 7C3 HuHd to NTSR1 as described in Example 3.

With high degrees of variations in the framework regions, 7C3 HdHd and 7C3 HdHu generated by grafting CDR sequences from mAb 7C3 MM show much lower binding signals for NTSR1 (in comparison with mAb 7C3 MM, 7C3 HuHu and 7C3 HuHd in binding ELISA) (FIG. 4).

Figure 5:
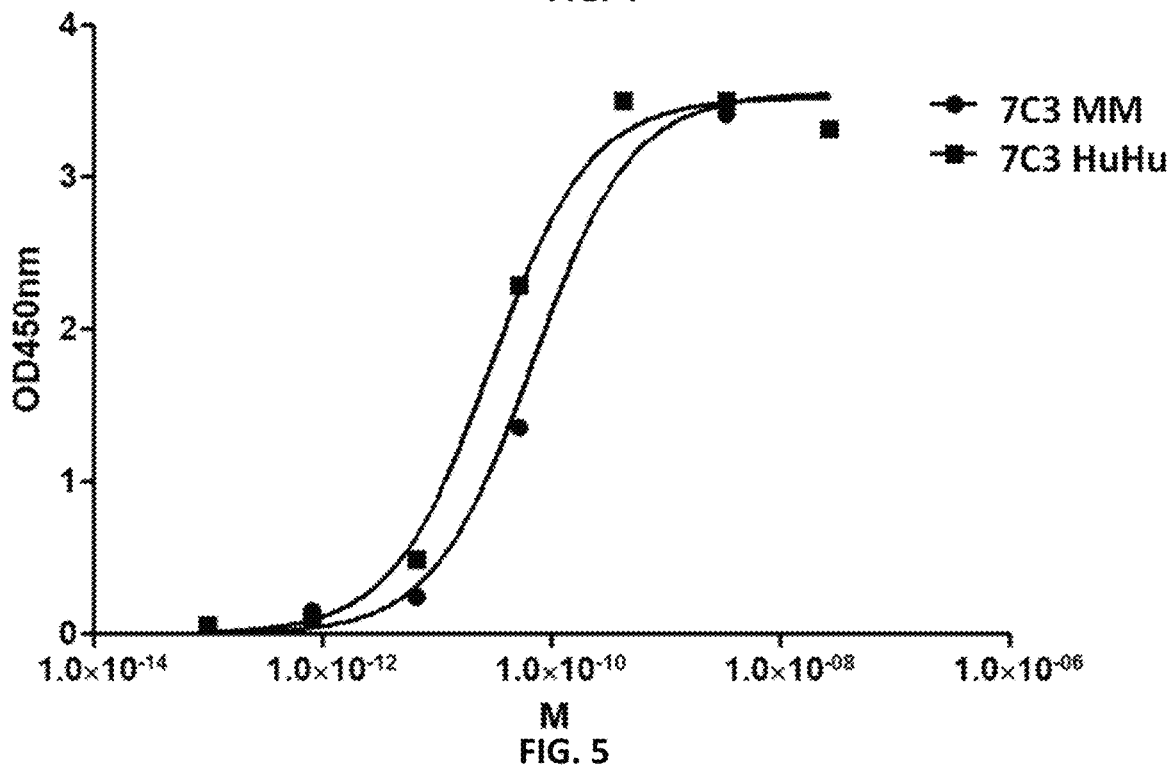
FIG. 5 depicts results of $K_d$ binding affinity analysis of the mouse-human chimera antibody 7C3 MM and the humanized antibody 7C3 HuHu to NTSR1. Detailed procedures of chimera antibody expression, purification and $K_d$ analysis are described in Example 3. The results show that $K_d$ of the humanized antibody 7C3 HuHu is not significant different from that of the mouse-human chimera antibody 7C3 MM.

In contrast to 7C3 HdV$_H$, with high degrees of variations in the framework regions, 7C3 HuV$_H$ generated by grafting CDR sequences from mAb 7C3 MM into IGHV1 framework sequences has good binding signal for NTSR1 whether pairing with 7C3 HuV$_L$ or 7C3 HdV$_L$ (7C3 HuHu and 7C3 HuHd vs. 7C3 HdHd and 7C3 HdHu in binding ELISA) (FIG. 4), and has relatively good affinity (7C3 HuHu, $K_D$=2.94×10$^{-10}$ M in comparison with mAB 7C3 MM, $K_D$=6.76×10$^{-10}$ M) (FIG. 5, Table 3).

TABLE 3

ELISA $K_D$ of 7C3 MM and 7C3 HuHu

| | ELISA $K_D$ (M) |
|---|---|
| 7C3 MM | 6.76 * 10$^{-10}$M |
| 7C3 HuHu | 2.94 * 10$^{-10}$M |

These results suggest that only IGHV1 heavy chain framework regions can tolerate a relatively high degree of variations without impacting the CDR region conformations.

Example 4

Fluorescence-Activated Cell Sorting (FACS)

Anti-NTSR1 antibodies were used to detect cells that express NTSR1 on the cell surfaces, for example using FACS. NTSR1 expressing cells, FaDu, were harvested and re-suspended in 5% PBS/FBS buffer. The cells (1×10$^5$) were incubated with anti-NTSR1 antibody (1-10 μg/ml) or negative control, at 4° C. for 1 hr, and then stained with goat anti-human IgG FITC conjugate (1/1000) at 4° C. for 1 hr. For each assay, two additional controls were prepared; one without primary antibody and the other one with absence of any antibody. All treated samples were analyzed with FACS-VERSE™ (BECTON DICKINSON®) and the results were processed by FACSUITE™ software (BECTON DICKINSON®).

The results are shown in Table 4. The chimeric anti-NTSR1 antibody (7C3 MM), and the humanized anti-NTSR1 antibodies 7C3 HuHu and 7C3 HuHd do not bind well to FaDu cells at concentration of 1 μg/mL. However, the chimeric anti-NTSR1 antibody (7C3 MM), and the humanized anti-NTSR1 antibodies 7C3 HuHu and 7C3 HuHd do not bind significantly to FaDu cells at concentration of 10 μg/mL.

TABLE 4

Cell-Binding Assays for Determining the Affinity of humanized antibodies by FACS

| Clone name | % Flow binding (10 ug/ml) | % Flow binding (1 ug/mL) |
|---|---|---|
| 7C3 MM | 91 | 31 |
| 7C3 HuHu | 98 | 64 |
| 7C3 HuHd | 99 | 73 |

Example 5

Affinity Maturation of Humanized Antibodies

The binding affinity of m7C3 to NTSR1 has been improved based on affinity maturation process, and the obtained clone is termed as AKT2. Compared with the sequence of m7C3, AKT2 has two mutations in heavy chain CDRs and one mutation in light chain CDRs, and shows an enhanced binding affinity to NTSR1. These three mutations are T28A (in CDRH1), Y96H (in CDRH3), and S92A (in CDRL3), which are shown as underlined residues in FIG. 6. Residues are numbered according to Kabat nomenclature.

Figure 7:
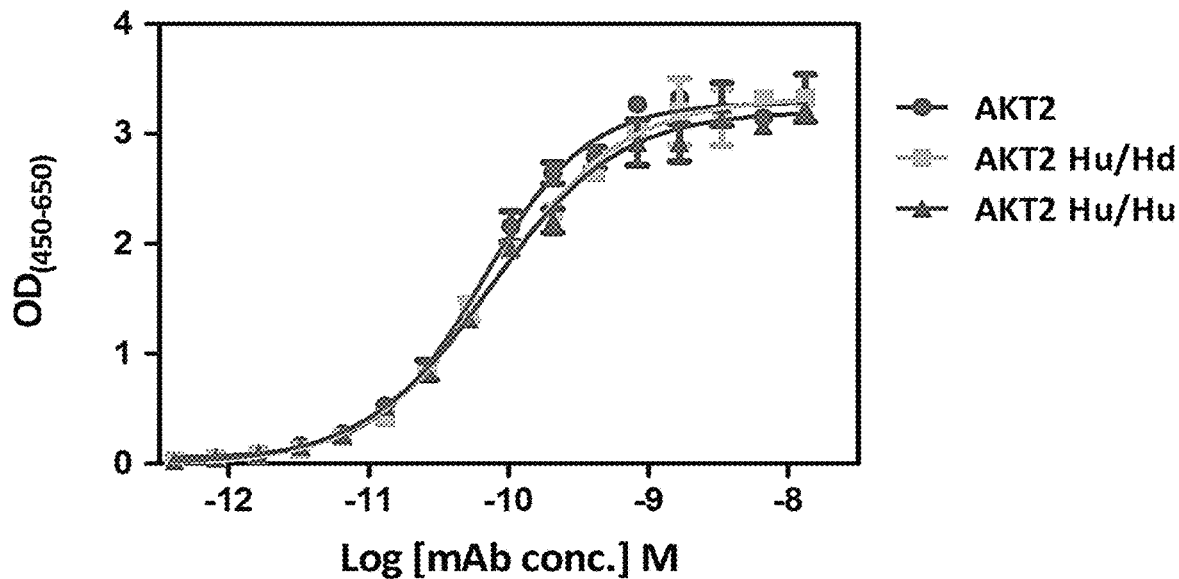
FIG. 7 depicts results of binding affinity analysis of the mouse-human chimera antibody AKT2, the humanized antibodies AKT2 HuHu and AKT2 HuHd to NTSR1. Detailed procedures of chimera antibody expression, purification and $K_d$ analysis are described in Example 5. The results show that $K_d$ of the humanized antibodies AKT2 HuHu and AKT2 HuHd are not significant different from that of the mouse-human chimera antibody AKT2.

To further enhance the binding affinity of 7C3 humanized antibodies to NTSR1, 7C3 HuHu and 7C3 HuHd were mutated to AKT2 HuHu and AKT2 HuHd, respectively (FIG. 6, Table 1 SEQ ID NO: 15 to SEQ ID NO: 17, Table 2). The mutation process was performed using gene synthesis technology. The results of ELISA show that the affinity of AKT2 HuHu and AKT2 HuHd to NTSR1 are similar to that of the original mouse antibody AKT2 (FIG. 7).

Example 6

Affinity Measurements and Kinetic Analysis

To know the binding kinetics differences among individual anti-NTSR1 antibodies, surface plasmon resonance (SPR) measurement with BIACORE™ T200 (CYTIVA® Inc.) was used as previously described (Karlsson & Falt, (1997) J. Immunol Methods 200:121-133). Carboxymethylated dextran biosensor chips (CM5, CYTIVA® Inc.) were activated with N-ethyl-N'-(3-dimethylaminopropyl)-carbodiimide hydrochloride (EDC) and N-hydroxysuccinimide (NHS) according to the supplier's instructions. NTSR1 protein was diluted with 10 mM sodium acetate, pH 4.0, into 5 μg/ml before injection at a flow rate of 10 μL/minute to achieve approximately 1500 response units (RU) of coupled protein followed by the injection of 1 M ethanolamine to block unreacted groups. For kinetics measurements, two-fold serial dilutions of anti-NTSR1 mAb (0.3125 nM to 40 nM) were injected in HBS-EP+BIACORET™ running buffer provided by the manufacturer (CYTIVA® Inc.) at 25° C. at a flow rate of 30 μL/min, and binding responses on the NTSR1 protein were corrected by subtraction of responses on a blank flow cell. Association rates ($k_{on}$ or $K_a$) and dissociation rates ($k_{off}$ or $K_d$) were calculated using a simple one-to-one Langmuir binding model with separate fittings of $k_{on}$ and $k_{off}$. (CYTIVA® BIACORET™ Insight Evaluation Software).

The results are shown in the Table 5. The $k_{on}$ and $k_{off}$ of chimera AKT2 mAb binding with NTSR1 are $4.068 \times 10^5$ and $6.558 \times 10^{-4}$, respectively, and $K_D$ is $1.612 \times 10^{-9}$ M. The $k_{on}$ and $k_{off}$ of AKT2 HuHu (with $V_H$ of IMGT edition, AKT2 HuV$_H$) binding with NTSR1 are $7.877 \times 10^5$ and $8.084 \times 10^{-4}$, respectively, and $K_D$ is $1.026 \times 10^{-9}$ M. The $k_{on}$ and $k_{off}$ of AKT2 HuHd (with $V_H$ of IMGT edition, AKT2 HuV$_H$) binding with NTSR1 are $4.614 \times 10^5$ and $6.575 \times 10^{-4}$, respectively, and $K_D$ is $1.425 \times 10^{-9}$ M.

TABLE 5

The Multi-cycle kinetic assay of anti-NTSR1 antibodies binding to NTSR1

|  | $K_a$(1/Ms) | $K_d$(1/s) | $K_D$(M) |
|---|---|---|---|
| AKT2 | $4.068 \times 10^5$ | $6.558 \times 10^{-4}$ | $1.612 \times 10^{-9}$ |
| AKT2 HuHu | $7.877 \times 10^5$ | $8.084 \times 10^{-4}$ | $1.026 \times 10^{-9}$ |
| AKT2 HuHd | $4.614 \times 10^5$ | $6.575 \times 10^{-4}$ | $1.425 \times 10^{-9}$ |

As shown in FIG. 7, it suggests that the humanized antibodies AKT2 HuHu and AKT2 HuHd can recognize the human NTSR1 protein, and after humanization, the IMGT edition $V_H$ (AKT2 HuV$_H$) results in affinity similar to that of the mouse antibody AKT2 whether pairing with HuV$_L$ or HdV$_L$.

Example 7

In Vivo Pharmacokinetic (PK) Analysis

This Example used Meso Scale Discovery (MSD) Electrochemiluminescent (ECL) method to conduct the PK analysis of the anti-NTSR1 antibodies αNTSR1 (AKT2), αNTSR1 (AKT2 Hu/Hu) and αNTSR1 (AKT2 Hu/Hd) in BALB/c mice samples. The MSD assay can measure both conjugated and unconjugated antibodies. As illustrated in this example, for total antibody assay (including conjugated and unconjugated antibodies), the plate is coated with goat anti-human IgG, which can capture all humanized antibodies (conjugated and unconjugated).

The mice were administered at a dose level of 5 mg/kg via the tail vein. Blood samples were then obtained at different time points for determining the concentrations of αNTSR1 (AKT2), αNTSR1 (AKT2 Hu/Hu) and αNTSR1 (AKT2 Hu/Hd) in mice by MESO QuickPlex SQ 120 method. The PK parameters of αNTSR1 (AKT2), αNTSR1 (AKT2 Hu/Hu) and αNTSR1 (AKT2 Hu/Hd) were analyzed by noncompartmental analysis using PHOENIX™ for WinNonlin Program, version 6.3.

Figure 8:
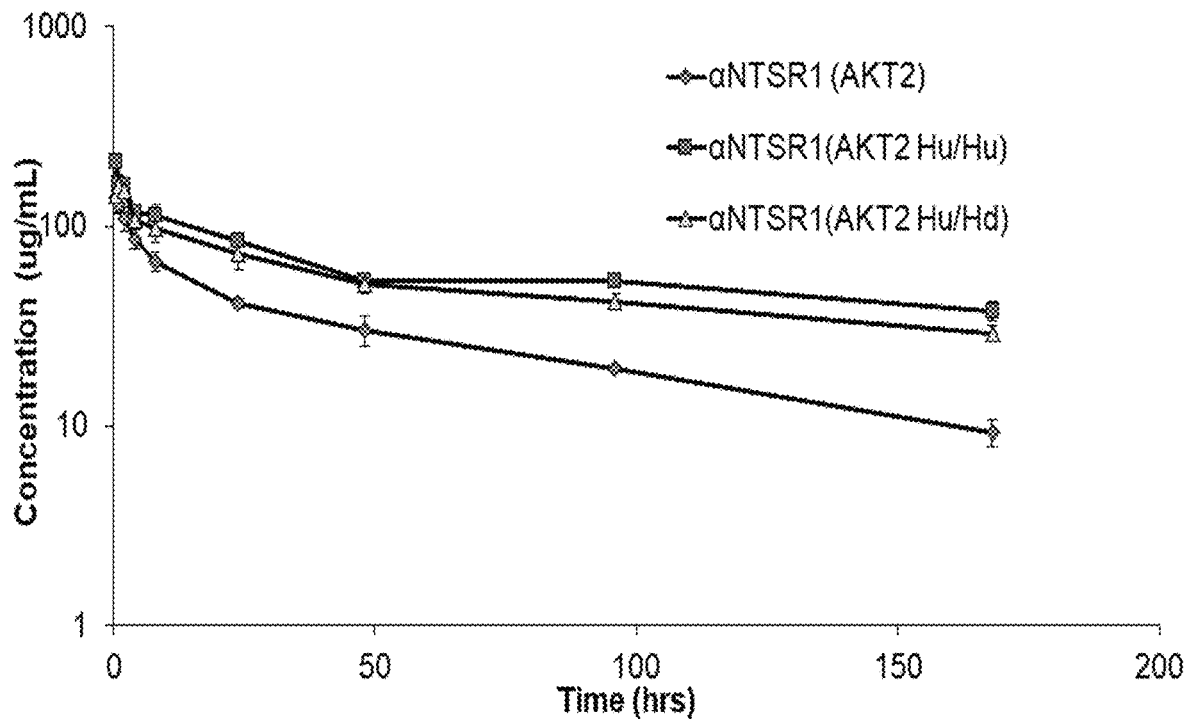
FIG. 8 shows results of in vivo pharmacokinetic analysis of the mouse-human chimera antibody AKT2, the humanized antibodies AKT2 HuHu and AKT2 HuHd in MSD assay.

Table 6 summarizes the results for the PK studies. The in vivo half live of αNTSR1 (AKT2) is 71.7±5.1 hrs; the half live of αNTSR1 (AKT2 Hu/Hu) is 182±90.8 hrs; and the half live of αNTSR1 (AKT2 Hu/Hd) is 156±48.6 hrs (FIG. 8).

Referring to the comparison of the total antibody pharmacokinetic profile of αNTSR1 (AKT2), αNTSR1 (AKT2 Hu/Hu) and αNTSR1 (AKT2 Hu/Hd), the half-life of the humanized antibodies αNTSR1 (AKT2 Hu/Hu) and αNTSR1 (AKT2 Hu/Hd) in BALB/c mice is 156-182 hours, which is significantly better than the 71 hours half-life of the mouse antibody αNTSR1 (AKT2). These properties would make the humanized antibodies αNTSR1 (AKT2 Hu/Hu) and αNTSR1 (AKT2 Hu/Hd) more useful as therapeutics.

Example 7

Internalization Assay

Figure 9A:
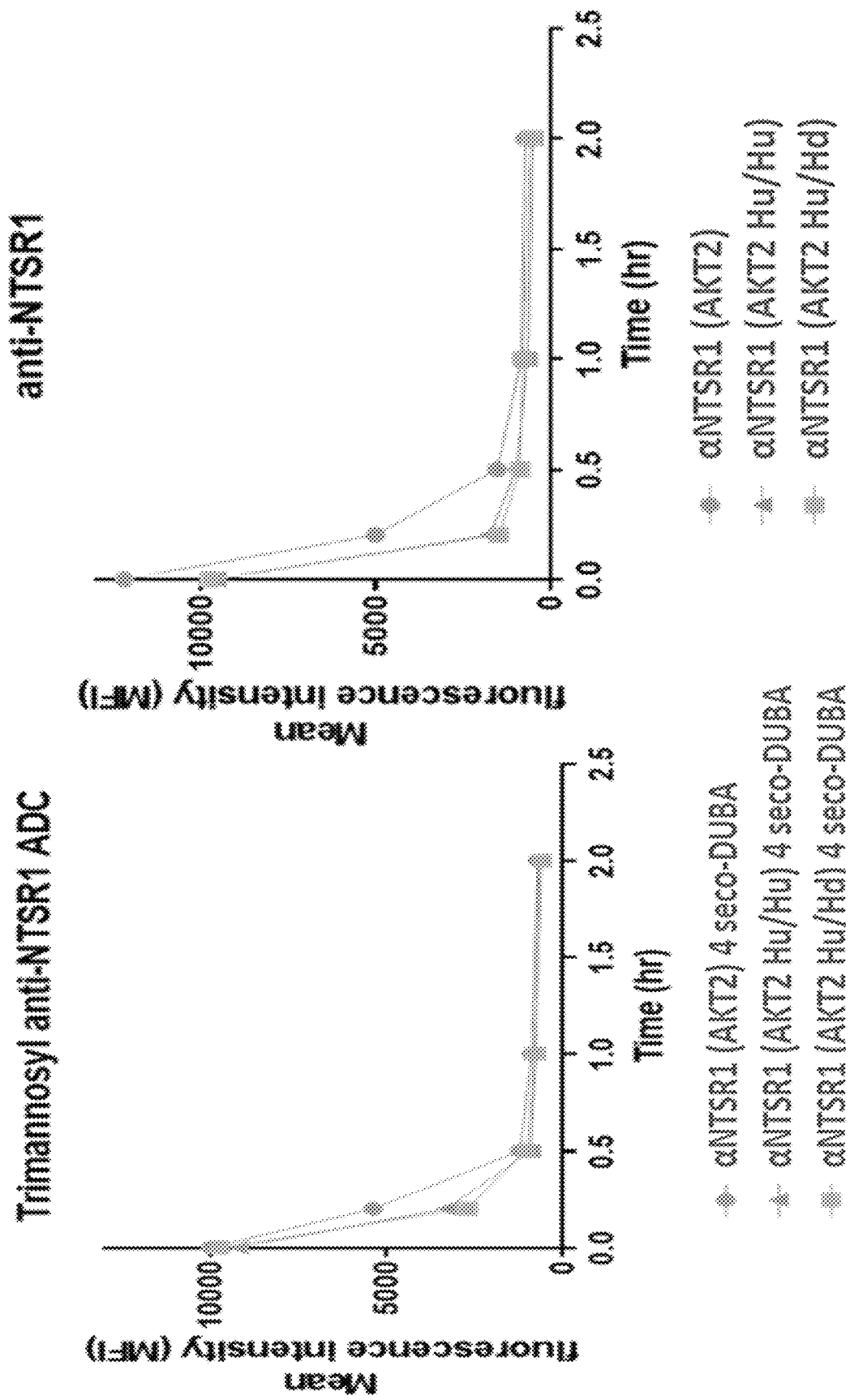
FIG. 9A shows internalization assay results of the mouse-human chimera AKT2, humanized antibodies AKT2 HuHu and AKT2 HuHd and the antibody-drug conjugates (ADCs) thereof in FaDu cells using Flow Cytometry (before normalization).
Figure 9B:
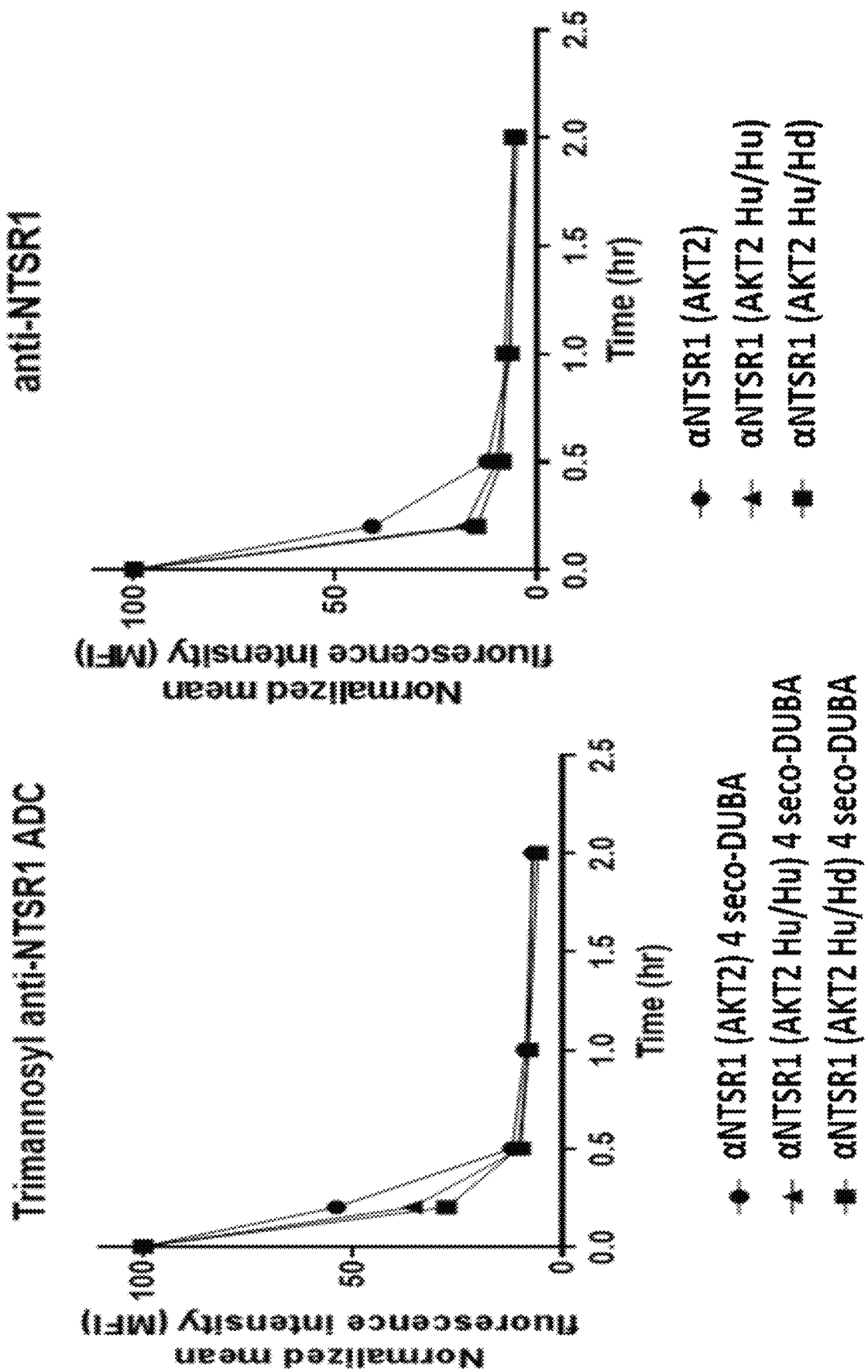
FIG. 9B shows a normalized result of FIG. 9A.

FaDu cells were trypsinized, and then harvested and resuspended in FAC buffer. Controls: secondary Ab antihuman IgG PE (1:200) was added to the FaDu cells. The cells were incubated at 4° C. for time intervals of 0, 0.5, 2, 5 and 24 hours, and then washed by 1 mL of FACS buffer. The supernatant was discarded. Testing groups: FaDu cells were pre-incubated with 10 μg/mL ADCs of trimannosyl and anti-NTSR1 antibodies αNTSR1 (AKT2), αNTSR1 (AKT2 Hu/Hu) and αNTSR1 (AKT2 Hu/Hd) in FACS buffer on ice for 60 min, washed three times with FACS buffer, and then incubated at 37° C. for time intervals of 0, 0.5, 2, 5 and 24 hours. The cells were analyzed by flow cytometry (BD LSRFORTESSA®) and the results are shown in FIG. 9.

Example 8

In Vitro Cytotoxicity Study

Figure 10:
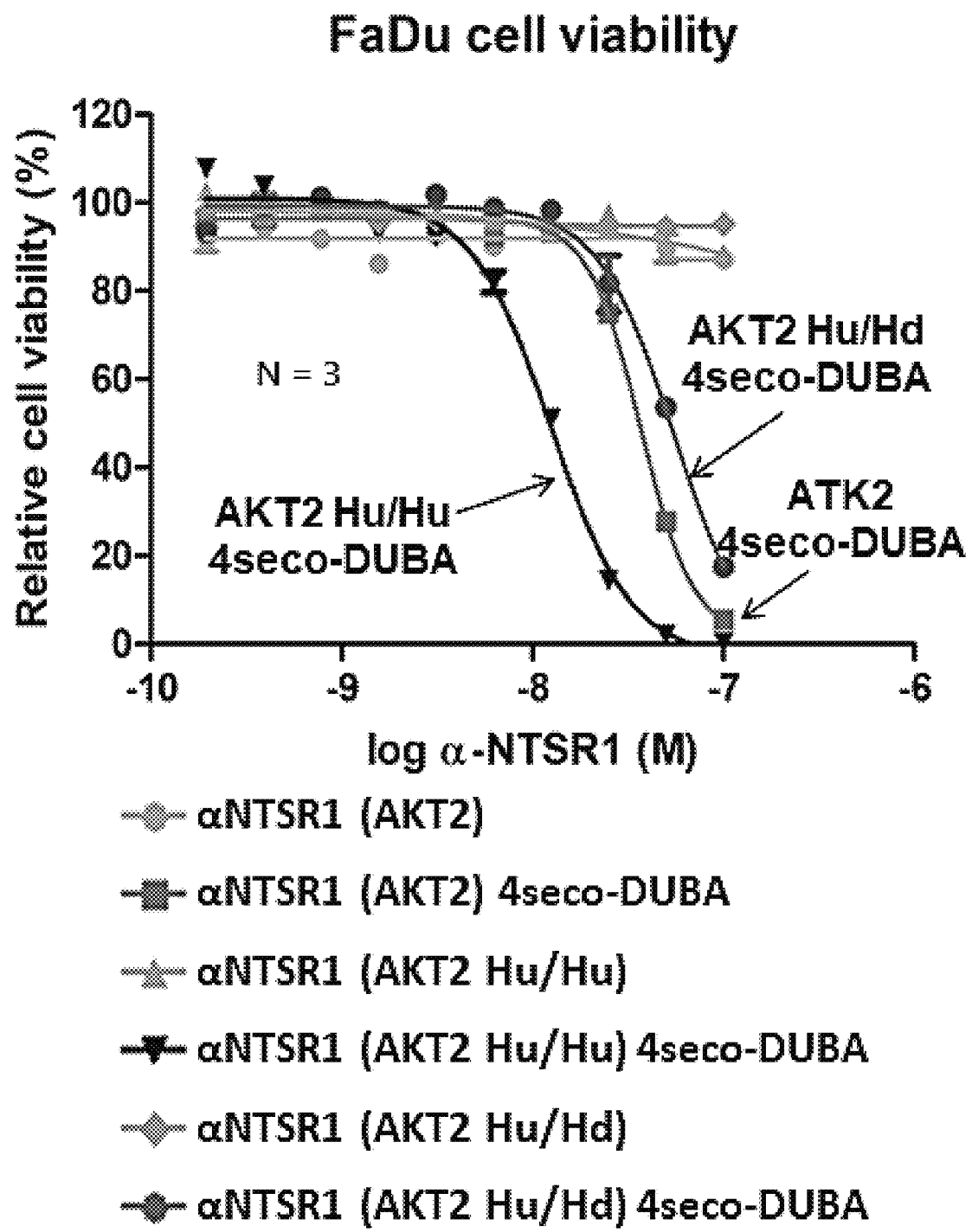
FIG. 10 shows cytotoxicity assay results of the mouse-human chimera antibody AKT2, the humanized antibodies AKT2 HuHu and AKT2 HuHd, and the ADCs thereof in FaDu cells.

Human head and neck cancer cell line FaDu was respectively grown in RPMI-1640 medium (ATCC® modification) supplemented with 10% fetal bovine serum. The FaDu cell lines were maintained in an atmosphere of 5% $CO_2$ in a humidified 37° C. incubator. The day before treatment, cells were collected and seeded into 96-well plates (4,000 cells per well). On the second day, cells were treated with 2-fold serial dilution concentration of toxic payloads and ADCs listed in Table 7. Each treatment was performed in eight triplicate data points. After the treatment of 72 hours, cell viability was assessed by CELLTITER-GLO® kit (PROMEGA®) according to the manufacturer's instruction. At the end of the incubation, luminescence was measured using a SpectraMax i3x Multi Mode Detection Platform (MOLECULAR DEVICES®). Compound cytotoxicity was evaluated in comparison to cells treated with 0.05% PBS (ADCs) or 0.05% DMSO (toxic payload). IC50 values were calculated by fitting viability data with a four-parameter logistic equation using GRAPHPAD® prism 5.0 software. The results are shown in Table 7 (FIG. 10).

TABLE 6

| Clone | C0 (mg/mL) | AUC(0-last) (mg × h/mL) | AUC(0-∞) (mg × h/mL) | MRT (h) | t½ (h) | CL (mL/min/Kg) | Vss (L/Kg) |
|---|---|---|---|---|---|---|---|
| AKT2 | 162 ± 44.5 | 4695 ± 300 | 5661 ± 464 | 89.6 ± 6.6 | 71.7 ± 5.1 | 0.030 ± 0.002 | 0.159 ± 0.010 |
| AKT2 Hu/Hu | 271 ± 46.7 | 10074 ± 331 | 20108 ± 5407 | 252 ± 116 | 182 ± 90.8 | 0.009 ± 0.002 | 0.120 ± 0.026 |
| AKT2 Hu/Hd | 146 ± 14.7 | 8591 ± 274 | 15253 ± 2452 | 209 ± 62.5 | 156 ± 48.6 | 0.011 ± 0.002 | 0.135 ± 0.020 |

TABLE 7

IC50 values of ADCs.

| Name | Relative IC50 (nM) |
|---|---|
| αNTSR1 (AKT2) | — |
| αNTSR1 (AKT2) 4seco-DUBA | 36.9 |
| αNTSR1 (AKT2 Hu/Hu) | — |
| αNTSR1 (AKT2 Hu/Hu) 4seco-DUBA | 12.51 |
| αNTSR1 (AKT2 Hu/Hd) | — |
| αNTSR1 (AKT2 Hu/Hd) 4seco-DUBA | 55.05 |

Example 9

Codon Optimization for CHO Cell Line

From the examples above, we prospect that the aforementioned anti-NTSR1 monoclonal antibodies have the potential for development as therapeutic antibodies.

To mass-produce the humanized therapeutic antibodies in the CHO cell line, codon optimization were performed by using the GENEOPTIMIZER® software tool. The variable regions of αNTSR1 (AKT2), αNTSR1 (AKT2 Hu/Hu) and αNTSR1 (AKT2 Hu/Hd) (Table 1, SEQ ID NO: 9 to SEQ ID NO: 10, and SEQ ID NO: 15 to SEQ ID NO: 17) were subjected to codon optimization to obtain the codon-optimized DNA segments for antibody expression in the CHO cell line. The optimization parameters include codon quality distribution (to select the most frequently used codon for the desired expression system) and GC content (to control the GC content within the desirable range).

Example 10

Development of Anti-NTSR1 Monoclonal Antibodies Expression in Stable CHO Cell Pools The codon-optimized DNA segments encoding the $V_H$ and $V_L$ of αNTSR1 (AKT2), αNTSR1 (AKT2 Hu/Hu) and αNTSR1 (AKT2 Hu/Hd) were directly generated by the nucleotide synthesis method, respectively. Then, the optimized DNA segments were respectively sub-cloned into a human HERCEPTINRFC® antibody expression vector pCHO-NTSR1, and the vectors were introduced into host cells to prepare recombinant antibody-expressing cells. As the host cells for expression, the CHOS cells (LIFE-TECHNOLOGY® Inc.) were used. The vector was introduced into the host cells by lipofectamine 2000 in accordance with the attached instruction manual (manufactured by INVITROGEN®.) About 2.5 µg of the antibody expression vector was linearized by restriction enzymes, the gene was introduced into $4\times10^6$ cells, and the cells were inoculated to a 6-well culture plate. For low concentration selection, the resultant cell pools were grown in the selection medium containing 10 µg/ml of puromycin and 100 nM of methotrexate or 20 µg/ml of puromycin and 200 nM of methotrexate. For further selection, the other stage of high concentration selection was performed. The primary selection pools were further grown in the medium containing 30 µg/ml of puromycin and 500 nM of methotrexate or in the medium containing 50 µg/ml of puromycin and 1000 nM of methotrexate.

The results are shown in Table 8. The productivity of αNTSR1 (AKT2), αNTSR1 (AKT2 HuHu), and αNTSR1 (AKT2 HuHd) were 20.49, 53.73, and 66.96 mg per liter after 5 days incubation, respectively. The result indicated that the productivity of the chimeric αNTSR1 (AKT2) antibody was significantly poor. However, the productivity of the humanized αNTSR1 (AKT2 Hu/Hu) and αNTSR1 (AKT2 Hu/Hd) antibodies were significantly improved and increased to 2.5-3 times after humanization.

TABLE 8

Antibodies expression levels from the generated CHO cell pools

| αNTSR1 antibody | Productivity 5D (mg/L) |
|---|---|
| αNTSR1 (AKT2) | 20.49 |
| αNTSR1 (AKT2 HuHu) | 53.73 |
| αNTSR1 (AKT2 HuHd) | 66.96 |

Example 11

Xenograft Model of Anti-NTSR1 ADCs (Head and Neck Cancer)

The aim of this study was to evaluate the in vivo antitumor efficacy of αNTSR1 (AKT2) 4seco-DUBA, αNTSR1 (AKT2 Hu/Hu) 4seco-DUBA, and αNTSR1 (AKT2 Hu/Hd) 4seco-DUBA in FaDu human head and neck cancer xenograft model in male NOD SCID mice.

Formulations respectively comprising test article αNTSR1 (AKT2) 4seco-DUBA, test article αNTSR1 (AKT2 Hu/Hu) 4seco-DUBA, test article αNTSR1 (AKT2 Hu/Hd) 4seco-DUBA, and Hu IgG were formulated by diluting the stock with a 25 mM sodium citrate buffer (pH 6.5). Each of the formulations was administered intravenously (IV) to the mice once weekly for three weeks.

The FaDu cells were maintained in vitro as a monolayer culture in RPMI-1640 medium supplemented with 10% fetal bovine serum at 37° C. in an atmosphere of 5% $CO_2$ in air. The tumor cells were routinely sub-cultured twice weekly by trypsin-EDTA treatment. The cells growing in an exponential growth phase were harvested and counted for tumor inoculation.

Male NOD SCID mice at age of 6-7 weeks were quarantined for one week. Five mice were housed in each cage. All animals were hosted in the animal facility with a 12-h light/12-h dark cycle at 19-25° C. Animals had free access to rodent pellet foods and water ad libitum.

FaDu cells were subcutaneously (SC) implanted ($4\times10^6$ cells in 1:1 PBS/matrigel mixture at 0.1 mL per mouse) into the right flank of male NOD SCID mice. When the average tumor volume had reached about 200 mm$^3$, the mice were randomly divided into 7 groups (N=6 per group). Each of Hu IgG, αNTSR1 (AKT2) 4seco-DUBA (5 mg/kg), αNTSR1 (AKT2 Hu/Hu) 4seco-DUBA (5 mg/kg), and αNTSR1 (AKT2 Hu/Hd) 4seco-DUBA (5 mg/kg) was intravenously administered twice weekly for 3 weeks.

The tumor volumes, body weights, mortality, and signs of overt toxicity were monitored and recorded three times weekly for 28 days. Tumor volumes (mm$^3$) were measured three times per week using calipers and calculated according to the formula: Tumor Volume=$(w^2 \times l)/2$, where w=width and l=length in diameter (mm) of the tumor. The percentages of tumor growth inhibition (TGI) were calculated using the following formula: % TGI=$[1-(T/C)]\times 100\%$, where T and C represent the mean tumor volumes of the treatment group and the control group, respectively. A TGI (%) value≥58% was considered as indicating significant anti-tumor activity. Animals were weighed three times weekly until the completion of the study.

Figure 11:
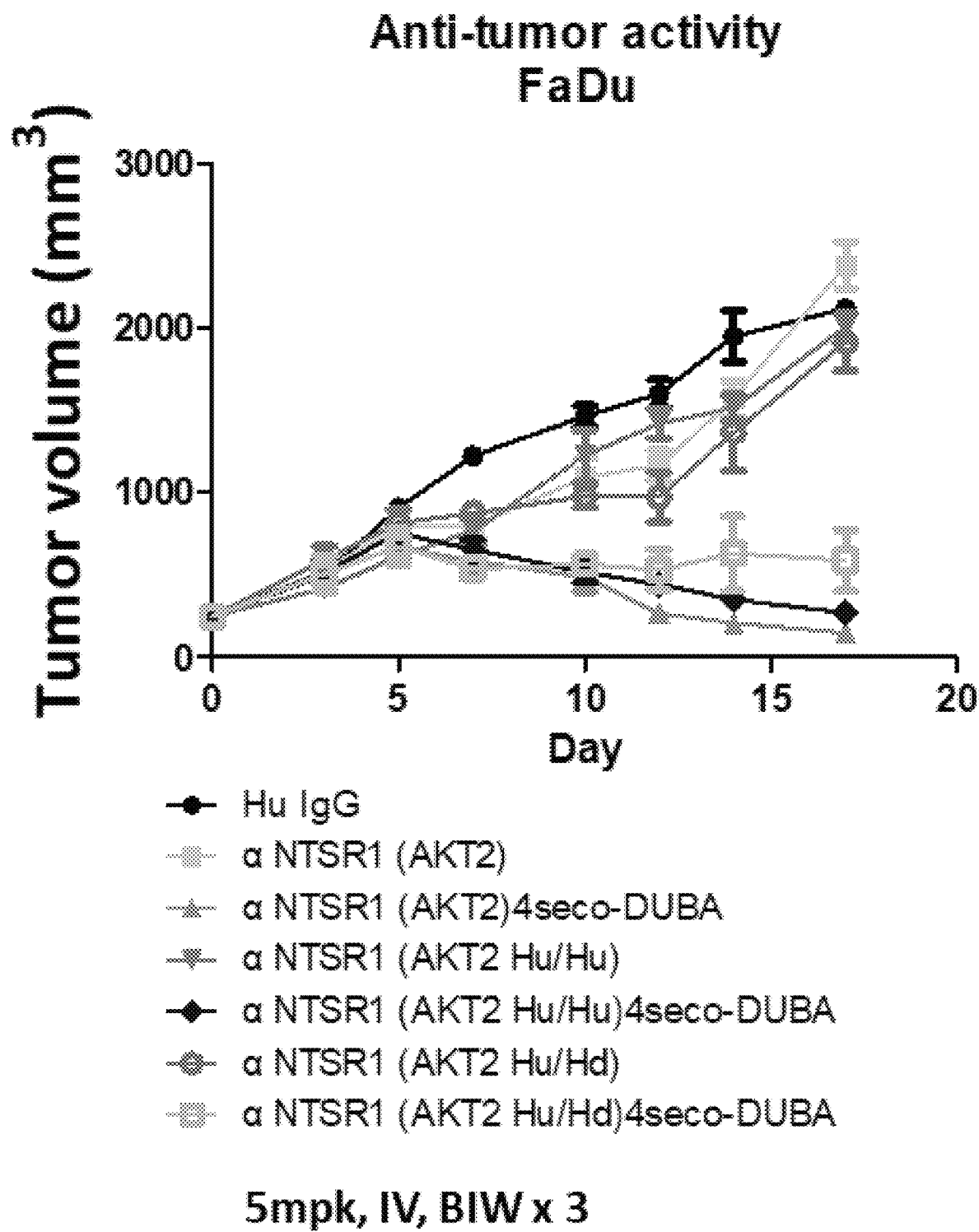
FIG. 11 depicts in vivo efficacy results of ADCs of the mouse-human chimera antibody AKT2, the humanized antibodies AKT2 HuHu and AKT2 HuHd in FaDu human head and neck cancer xenografts.

FIG. 11 shows the tumor growth curve in FaDu implanted male NOD SCID mice. The TGI values are shown in Table 9. The results indicate that αNTSR1 (AKT2) 4seco-DUBA (5 mg/kg), αNTSR1 (AKT2 Hu/Hu) 4seco-DUBA (5 mg/kg), and αNTSR1 (AKT2 Hu/Hd) 4seco-DUBA (5 mg/kg) significantly reduced FaDu tumor growth from Day 10 to Day 17.

TABLE 9

In vivo anticancer study

| Treatment (5 mpk, IV, BIW × 3) | TGI % (1-T/C) | | | | | | | |
|---|---|---|---|---|---|---|---|---|
| | Day 0 | Day 3 | Day 5 | Day 7 | Day 10 | Day 12 | Day 14 | Day 17 |
| Vehicle (human IgG1) | 0.0 | 0.0 | 0.0 | 0.0 | 0.0 | 0.0 | 0.0 | 0.0 |
| αNTSR1(AKT2) mAb | 0.0 | (3.5) | 11.1 | 34.8 | 31.0 | 31.1 | 29.9 | 21.6 |
| αNTSR1(AKT2) 4seco-DUBA | 0.0 | (0.9) | 28.5 | 54.4 | 68.5 | 83.8 | 90.5 | 95.3 |
| αNTSR1(AKT2 Hu/Hu) mAb | 0.0 | 17.7 | 33.4 | 37.3 | 13.4 | 6.7 | 25.6 | 26.9 |
| αNTSR1(AKT2 Hu/Hu) 4seco-DUBA | 0.0 | (0.2) | 17.5 | 47.2 | 65.4 | 72.2 | 83.8 | 90.8 |
| αNTSR1(AKT2 Hu/Hd) mAb | 0.0 | (11.7) | 13.1 | 28.4 | 36.2 | 40.9 | 37.8 | 32.5 |
| αNTSR1(AKT2 Hu/Hd) 4seco-DUBA | 0.0 | 6.6 | 29.8 | 56.1 | 60.9 | 62.7 | 65.2 | 76.6 |

The invention claimed is:

1. A humanized anti-NTSR1 antibody or antigen-binding fragment, wherein (a) the VH comprises the sequence of SEQ ID NO: 16, and the VL comprises the sequence of SEQ ID NO: 17 or 15; (b) the VH comprises the sequence of SEQ ID NO: 13, and the VL comprises the sequence of SEQ ID NO: 12 or 14; or (c) the VH comprises the sequence of SEQ ID NO: 11, and the VL comprises the sequence of SEQ ID NO: 12 or 14.

2. The humanized anti-NTSR1 antibody or the antigen-binding fragment thereof of claim 1, wherein the humanized anti-NTSR1 antibody has a heavy chain constant region selected from the group consisting of IgG1, IgG2 and IgG4 isoforms, and a light chain constant region selected from the group consisting of κ and λ isotypes.

3. The humanized anti-NTSR1 antibody or the antigen-binding fragment thereof of claim 1, which is an Fab fragment, an F(ab')$_2$ fragment, an ScFv fragment, or a chimeric antibody.

4. The humanized anti-NTSR1 antibody or the antigen-binding fragment thereof of claim 1, which is multi-specific.

5. An antibody conjugate, comprising:
the humanized anti-NTSR1 antibody or the antigen-binding fragment thereof of claim 1; and
a therapeutic agent conjugated with the humanized anti-NTSR1 antibody or the antigen-binding fragment thereof.

6. The antibody conjugate of claim 5, wherein the therapeutic agent is selected from the group consisting of antimetabolites, alkylating agents, alkylating-like agents, DNA minor groove alkylating agents, anthracyclines, antibiotics, calicheamicins, antimitotic agents, topoisomerase inhibitors, HDAC inhibitor, proteasome inhibitors, and radioisotopes.

7. The antibody conjugate of claim 5, wherein the therapeutic agent is mertansine (DM1), monomethyl auristin E (MMAE), seco-DUBA, exactecan, deruxtecan or monomethyl auristatin F (MMAF).

8. A vector encoding the humanized anti-NTSR1 antibody or the antigen-binding fragment thereof of claim 1.

9. A genetically engineered cell containing the vector of claim 8.

10. A genetically engineered cell expressing the humanized anti-NTSR1 antibody or the antigen-binding fragment of claim 1.

11. The genetically engineered cell of claim 10, which is an immune cell.

12. The genetically engineered cell of claim 10, which is a T cell.

13. A method for manufacturing the humanized anti-NTSR1 antibody or the antigen-binding fragment thereof claim 1, comprising: (a) introducing into a host cell one or more polynucleotides encoding the humanized anti-NTSR1 antibody or the antigen-binding fragment thereof; (b) culturing the host cell under conditions favorable to expression of the one or more polynucleotides; and (c) optionally, isolating the humanized anti-NTSR1 antibody or the antigen-binding fragment thereof from the host cell and/or a medium in which the host cell is grown.

14. A pharmaceutical composition, comprising:
an effective amount the humanized anti-NTSR1 antibody or the antigen-binding fragment thereof of claim 1; and
a pharmaceutically acceptable carrier.

15. A method for treating a disease and/or disorder caused by or related to NTSR1 activity and/or signaling in a subject in need of such treatment, comprising administering to the subject an effective amount of the humanized anti-NTSR1 antibody or the antigen-binding fragment thereof of claim 1; and a pharmaceutically acceptable carrier.

16. The method of claim 15, wherein the disease is a cancer.

17. The method of claim 16, wherein the cancer is a head and neck cancer, lung cancer, liver cancer, gastric cancer, pancreatic cancer, breast cancer, prostate cancer or colorectal cancer.

18. A method for detecting NTSR1 in a sample, comprising contacting the sample with the humanized anti-NTSR1 antibody or the antigen-binding fragment thereof of claim 1.

19. A kit for detecting NTSR1 in a sample, comprising the humanized anti-NTSR1 antibody or the antigen-binding fragment thereof of claim 1.

* * * * *